US011401231B2

(12) United States Patent
Lee et al.

(10) Patent No.: US 11,401,231 B2
(45) Date of Patent: Aug. 2, 2022

(54) STILBENE DERIVATIVE AND METHOD FOR PREPARING SAME

(71) Applicant: Ozchela Inc., Seoul (KR)

(72) Inventors: Min-Kyung Lee, Seoul (KR); Jin-Kak Lee, Hwaseong-si (KR); Won-Seok Han, Gwangmyeong-si (KR)

(73) Assignee: OZCHELA INC., Seoul (KR)

( * ) Notice: Subject to any disclaimer, the term of this patent is extended or adjusted under 35 U.S.C. 154(b) by 17 days.

(21) Appl. No.: 16/338,442

(22) PCT Filed: Sep. 29, 2017

(86) PCT No.: PCT/KR2017/010998
§ 371 (c)(1),
(2) Date: Mar. 29, 2019

(87) PCT Pub. No.: WO2018/062953
PCT Pub. Date: Apr. 5, 2018

(65) Prior Publication Data
US 2019/0248729 A1 Aug. 15, 2019

(30) Foreign Application Priority Data

Sep. 30, 2016 (KR) .................. 10-2016-0127050
Aug. 14, 2017 (KR) .................. 10-2017-0102983

(51) Int. Cl.
| | | |
|---|---|---|
| *C07C 63/331* | (2006.01) | |
| *C07D 241/04* | (2006.01) | |
| *A61K 31/235* | (2006.01) | |
| *A61K 31/277* | (2006.01) | |
| *A61K 31/4453* | (2006.01) | |
| *A61K 31/495* | (2006.01) | |
| *A61K 31/5375* | (2006.01) | |
| *C07D 295/192* | (2006.01) | |
| *C07C 255/41* | (2006.01) | |
| *C07D 295/155* | (2006.01) | |
| *C07C 253/30* | (2006.01) | |
| *C07C 255/35* | (2006.01) | |
| *C07D 213/80* | (2006.01) | |
| *C07C 255/37* | (2006.01) | |
| *C07C 255/42* | (2006.01) | |
| *C07D 213/79* | (2006.01) | |
| *C07C 229/68* | (2006.01) | |
| *C07D 207/08* | (2006.01) | |
| *C07D 221/00* | (2006.01) | |
| *C07D 265/30* | (2006.01) | |

(52) U.S. Cl.
CPC .......... *C07C 63/331* (2013.01); *A61K 31/235* (2013.01); *A61K 31/277* (2013.01); *A61K 31/4453* (2013.01); *A61K 31/495* (2013.01); *A61K 31/5375* (2013.01); *C07C 229/68* (2013.01); *C07C 253/30* (2013.01); *C07C 255/35* (2013.01); *C07C 255/37* (2013.01); *C07C 255/41* (2013.01); *C07C 255/42* (2013.01); *C07D 207/08* (2013.01); *C07D 213/79* (2013.01); *C07D 213/80* (2013.01); *C07D 221/00* (2013.01); *C07D 241/04* (2013.01); *C07D 265/30* (2013.01); *C07D 295/155* (2013.01); *C07D 295/192* (2013.01)

(58) Field of Classification Search
CPC .................................................. C07C 63/331
See application file for complete search history.

(56) References Cited

U.S. PATENT DOCUMENTS

| | | | | |
|---|---|---|---|---|
| 2006/0205792 A1* | 9/2006 | Wong | ................... | C07D 311/36 514/352 |
| 2009/0325930 A1* | 12/2009 | Hamaoka | ............. | C07D 213/64 514/213.01 |
| 2012/0165567 A1 | 6/2012 | Sharma et al. | | |
| 2012/0251581 A1 | 10/2012 | Gregory et al. | | |
| 2014/0336136 A1* | 11/2014 | Bitzer | ...................... | A61K 8/37 514/25 |

FOREIGN PATENT DOCUMENTS

| | | |
|---|---|---|
| CN | 1817863 A | 8/2006 |
| CN | 104193596 A | 12/2014 |
| CN | 105503652 A | 4/2016 |
| JP | 2003-020477 A | 1/2003 |
| WO | 2013/072390 A2 | 5/2013 |
| WO | 2015/078775 A2 | 6/2015 |
| WO | 2016/042318 A1 | 3/2016 |

OTHER PUBLICATIONS

Pinedo et al. (2000) McMahon et al (2000).*
Martinez et al., J.Med. Chem. (2004), 47, pp. 1136-1148.*
Azmi et al., Int. J. Mol. Sci, (2013).*
Alam et al., EJMC (2013) 790-797.*
Li et al., Green Chemistry (2012), 14(10), 2706-2709.*
Arockiam et al., Green Chemistry (2011), 13(11), 3075-3078.*
Umeda et al., Journal of Organic Chemistry (2009), 74(18), 7094-7099.*
Extended European Search Report of corresponding European Patent Application No. 17856839.0—10 pages (dated Apr. 24, 2020).
Merckx, "Sur quelques produits de condensation de systemes a methylene actif avec les aldehydes", Bulletin des Societes Chimiques Belges: Vlaamse Chemische Vereniging, vol. 58, No. 10-12—12 pages (1949).

(Continued)

Primary Examiner — Paul V Ward
(74) Attorney, Agent, or Firm — Morgan, Lewis & Bockius LLP

(57) ABSTRACT

This invention relates to a stilbene derivative and a method of preparing the same, and more particularly to a novel stilbene derivative for inhibiting the function of cyclophilin, which is effective at the prevention of cyclophilin-related diseases or at the treatment of symptoms of such diseases, and to a method of preparing the same.

5 Claims, No Drawings

(56) References Cited

OTHER PUBLICATIONS

Rorig, "Condensations of Substituted Benzaldehydes with m- or p-Acetylphenylacetonitrile 1", Journal of the American Chemical Society, vol. 75, No. 21—3 pages (Jun. 5, 1953).
Parveen et al., "Stereoselective synthesis of Z-acrylonitrile derivatives: catalytic and acetylcholinesterase inhibition studies", New Journal of Chemistry, vol. 38, No. 4—13 pages (2014).
Youn et al., "Bi(OTF)3-mediated intramolecular hydroamination of 2-aminostilbenes for the synthesis of 2-arylindolines", Tetrahedron, vol. 72, No. 32—8 pages (Jun. 2016).
Kiyama et al., "Novel Angiotensin II Receptor Antagonists. Design, Synthesis, and in Vitro Evaluation of Dibenzo(a,d) cycloheptene and Dibenzo(b,f)oxepin Derivatives. Searching for Bioisosteres of Biphenylyltetrazole Using a Three-Dimensional Search Technique", Journal of Medicinal Chemistry, vol. 38—15 pages (1995).
Harwood et al., "3-(4-Chlorophenyl)-2-(4-diethylaminoethoxyphenyl)-A-pentenonitrile Monohydrogen Citrate and Related Analogs", Biochemical Pharmacology, vol. 53—27 pages (1997).
Stewart et al., "The effect of substituents on the Lewis acidity of a-cyanostilbenes", Canadian Journal of Chemistry, vol. 45—4 pages (1967).
Office Action of corresponding Japanese Patent Application No. 2019-517944—14 pages (dated Apr. 14, 2020).
Prior Art Search Report for Expedited Examination submitted to Korean Patent Office—4 pages.
Stock et al., "Structure-behavior study of a family of "hybridcyanine" dyes which exhibit inverted solvatochromism", Physical Chemistry Chemical Physics, Issue 47—10 pages (2016).
Mukherjee et al., "Oxidative stress plays major role in mediating apoptosis in filarial nematode Setaria cervi in the presence of trans-stilbene derivatives", Free Radical Biology and Medicine, vol. 93—15 pages (2016).
Azmi et al., "Design, Synthesis and Cytotoxic Evaluation of o-Carboxamido Stilbene Analogues", International Journal of Molecular Sciences, vol. 14—21 pages (2013).
Alam et al., "Synthesis and Evaluation of (Z)-2,3-diphenylaerylonitrile Analogs as Anti-cancer and Anti-microbial Agents", European Journal of Medicinal Chemistry, vol. 69 (2013).
Martinez et al., "Benzo[f]azino[2,1-a]phthalazinium Cations: Novel DNA Intercalating Chromophores with Antiproliferative Activity", Journal of Medicinal Chemistry, vol. 47, No. 5—13 pages (2004).
International Search Report of corresponding Patent Application No. PCT/KR2017/010998—6 pages (dated Jan. 22, 2018).
Japanese Office Action for Japanese Patent Application No. 2020-168290, dated Sep. 7, 2021.
Australian Examination Report for Australian Patent Application No. 2020233773, dated Dec. 16, 2021.
Fuson et al., "Bimolecular Reduction of Hindered Aldehydes", Journal of the American Chemical Society (1942), vol. 64, pp. 30-33.
Ghizzoni et al., "6-Alkylsalicylates are Selective Tip60 Inhibitors and Target the Acetyl-CoA Binding Site", European Journal of Medicinal Chemistry (2012), 47(1), pp. 337-344.
Luderer et al., "Generation and Conversion of the Transient 1,1-bis(trimethylsilyl)-2-(2,4,6-triisopropylphenyl)-silene", Journal of Organometallic Chemistry (1996), vol. 510, pp. 181-188.
Nomura et al., "Styrylphenylphthalimides as Novel Transrepression-Selective Liver X Receptor (LXR) Modulators", ACS Medicinal Chemistry Letters (2015), 6(8), pp. 902-907.
Okazaki et al., "2,4,6-Tri-tert-butylselenobenzaldehyde, the First Stable Selenoaldehyde", Journal of the American Chemical Society (1989), 111(15), pp. 5949-5951.
Peat et al., "Interrogating HIV Integrase for Compounds that Bind—A SAMPL Challenge", Journal of Computer-Aided Molecular Design (2014), 28(4), pp. 347-362.
Shahzad et al., "Selenium-Mediated Synthesis of Biaryls through Replacement", Organic Letters (2010), 12(6), pp. 1364-1367.

* cited by examiner

STILBENE DERIVATIVE AND METHOD FOR PREPARING SAME

TECHNICAL FIELD

The present invention relates to a novel stilbene derivative for inhibiting the function of cyclophilin, which has an improved pharmaceutical profile, and to a method of preparing the same.

BACKGROUND OF THE INVENTION

Cyclophilin is known to be an effective drug target for many diseases, including viral infection diseases such as hepatitis B virus (HBV), hepatitis C virus (HCV), human immunodeficiency virus (HIV), influenza virus, etc.; diseases caused by inflammatory responses, such as cardiovascular diseases; rheumatoid arthritis; sepsis; asthma; periodontitis; aging; alopecia; neurodegenerative diseases caused by mitochondrial dysfunction; cancer and the like (Nigro P, et al, Cell Death Dis 2013, 4, e888).

Cyclophilin (CyP), which is a protein belonging to the immunophilin family, is found in all cells of all organisms, both prokaryotes and eukaryotes, and has been structurally well preserved throughout evolution. A human contains a total of 16 intrinsic proteins present therein, including seven main CyPs, namely CyP A, CyP B, CyP C, CyP D, CyP E, CyP 40, and CyP NK.

Cyclophilin is found in most cells in the human body, and CyP A and CyP 40 in mammals have cytoplasmic signal sequences, whereas CyP B and CyP C have N-terminal signal sequences that target to the endoplasmic reticulum. CyP D has a signal sequence that directs to mitochondria, CyP E has an amino-terminal RNA binding domain and is located in the nucleus, and CyP 40 has a TPR and is located in the cytoplasm. Human CyP NK is the largest CyP, with a large hydrophilic and positively charged carboxyl end, and is located in the cytoplasm.

Cyclophilin is a multifunctional protein involved in cellular processes and is responsible for essential functions in cells. Cyclophilin has been proven to have enzymatic properties of catalyzing cis-trans isomerization of peptidyl-prolyl bonds. Thus, cyclophilin is referred to as peptidyl prolyl cis-trans isomerase (PPIase), which may act as an acceleration factor in proper folding of newly synthesized proteins. PPIase is also involved in repairing damaged proteins due to environmental stresses, including thermal stress, ultraviolet radiation, changes in the pH of the cellular environment, and oxidant treatment. This function is known as molecular chaperone activity. The PPIase activity of cyclophilin has also been proven to be involved in intracellular protein trafficking, mitochondrial function and pre-mRNA processing.

Cyclosporine, one of available cyclophilin inhibitors, binds in the hydrophobic pocket of CyP A to thus inhibit PPIase activity. CyP A is a prototype of the cyclophilin family, and shows very high sequence homology with CyP B, CyP C, and CyP D in humans. The binding pockets of all cyclophilins are formed by approximately 109 amino acids, corresponding to highly conserved regions, and the sequence homology between CyP A and CyP D is 100%. Therefore, CyP A binding affinity is the best predictor of CyP D binding affinity and vice versa.

Such sequence homology between cyclophilins suggests that not only CyP D but also all cyclophilins are potential targets for functional inhibitors having binding affinity to CyP A, indicating that functional inhibitors of CyP A may be useful for the treatment of many diseases caused by numerous intracellular processes to which cyclophilins are related.

DETAILED DESCRIPTION OF THE INVENTION

Accordingly, the present invention is intended to provide a compound for inhibiting the function of cyclophilin, which has an improved pharmaceutical profile so as to prevent diseases, including viral infection diseases such as HBV, HCV, HIV, influenza and the like, cardiovascular diseases, rheumatoid arthritis, sepsis, asthma, periodontitis, aging, alopecia, neurodegenerative diseases, cancer, etc. or to treat symptoms of such diseases, and also to provide a method of preparing the same.

Therefore, the present invention provides a compound that is capable of inhibiting the function of cyclophilin. The present invention provides a stilbene derivative, represented by Chemical Formula 1 below, a pharmaceutically acceptable salt, a hydrate, a hydrated salt, a polymorphic crystal structure, a racemate, a diastereoisomer, or an enantiomer thereof. It is used for the prevention of cyclophilin-related diseases or for the treatment of symptoms of such diseases.

[Chemical Formula 1]

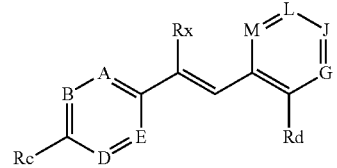

In Chemical Formula 1,
A is CRa or N,
B is CRb or N,
G is CRe or N,
J is CRf or N,
M is CRg or N,
D, E, and L are CRh or N,
Rx is H, $CH_3$, CN, $NH_2$, F, Cl, Br or I,
wherein when Rx is H, $CH_3$, $NH_2$, F, Cl, Br or I,
Ra is hydrogen, $NO_2$, CN, OH, a C1-C5 alkyl group, a C2-C10 alkenyl group, a C1-C2 alkoxy group, —COOR1 (R1 is hydrogen or a C1-C5 alkyl group) or —OCOR2 (R2 is a C1-C5 alkyl group),
Rb is hydrogen, a C1-C20 alkyl group, a C2-C10 alkenyl group, a C1-C10 alkoxy group, —COOR1 (R1 is hydrogen or a C1-C5 alkyl group) or —OCOR2 (R2 is a C1-C5 alkyl group),
Rc is OH, $NO_2$, a C1-C20 alkyl group, a C3-C10 cycloalkyl group, a C2-C10 alkoxy group, a C6-C12 aryl, a C5-C12 heterocyclic group, —NR3R4 (R3 is hydrogen, a C1-C20 alkyl group or a C6-C12 aryl, R4 is hydrogen, a C1-C20 alkyl group or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)$_2$R9 (R9 is a C6-C12 aryl or a C5-C12 heterocyclic group), or —COR10 (R10 is a C1-C20 alkyl group, a C6-C12 aryl, a C3-C10 cycloalkyl group or a C5-C12 heterocyclic group), Rd is halogen, NO₂, COOH, CN, a C2-C20 alkyl group, a C3-C10 cycloalkyl group, a C1-C10 alkoxy group, a C6-C12 aryl, a C5-C12 heterocyclic group, —NR3R4 (R3 is hydrogen, a C1-C20 alkyl or a C6-C12 aryl, R4 is hydrogen, a C1-C20 alkyl or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)₂R9 (R9 is a C6-C12 aryl or a C5-C12 heterocyclic group), or COR10 (R10 is a C1-C20 alkyl group, a C6-C12 aryl, a C3-C10 cycloalkyl group or a C5-C12 heterocyclic group), Re is hydrogen, NH₂, OH, CN, a C1-C20 alkyl group, a C2-C10 alkenyl group, a C1-C10 alkoxy, a C6-C12 aryl, a C5-C12 heterocyclic group, —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group) or —NHS(O)₂R9 (R9 is a C6-C12 aryl or a C5-C12 heterocyclic group), Rf is hydrogen, NH₂, OH, NO₂, a C1-C4 alkyl group, a C2-C10 alkenyl group, a C1-C4 alkoxy group, a C6-C12 aryl, a C5-C12 heterocyclic group, —NHR11 (R11 is a C1-C2 alkyl group), —COOR12 (R12 is a C1-C2 alkyl group), —OCOR13 (R13 is a C1-C2 alkyl group), or —COR14 (R14 is a C1-C2 alkyl group), Rg is hydrogen, NH₂, OH, halogen, NO₂, COOH, CN, a C1-C20 alkyl group, a C2-C10 alkenyl group, a C3-C10 cycloalkyl group, a C1-C10 alkoxy group, a C6-C12 aryl, a C5-C12 heterocyclic group, —NR3R4 (R3 is hydrogen, a C1-C20 alkyl or a C6-C12 aryl, R4 is hydrogen, a C1-C20 alkyl or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)₂R9 (R9 is a C6-C12 aryl or a C5-C12 heterocyclic group), or —COR10 (R10 is a C1-C20 alkyl group, a C6-C12 aryl, a C3-C10 cycloalkyl group or a C5-C12 heterocyclic group), and Rh is hydrogen, NH₂, OH, a C1-C5 alkyl group or a C2-C10 alkenyl group, when Rx is CN, Ra is hydrogen, Rb is hydrogen, a C1-C20 alkyl group, a C2-C10 alkenyl group, a C1-C10 alkoxy group, —COOR1 (R1 is hydrogen or a C1-C5 alkyl group) or —OCOR2 (R2 is a C1-C5 alkyl group), Rc is OH, NO₂, a C1-C20 alkyl group, a C3-C10 cycloalkyl group, a C2-C10 alkoxy group, a C6-C12 aryl, a C5-C12 heterocyclic group, —NR3R4 (R3 is hydrogen, a C1-C20 alkyl group or a C6-C12 aryl, R4 is hydrogen, a C1-C20 alkyl group or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)₂R9 (R9 is a C6-C12 aryl or a C5-C12 heterocyclic group), or —COR10 (R10 is a C1-C20 alkyl group, a C6-C12 aryl, a C3-C10 cycloalkyl group, or a C5-C12 heterocyclic group), Rd is hydrogen, halogen, NO₂, COOH, CN, a C2-C20 alkyl group, a C3-C10 cycloalkyl group, a C1-C10 alkoxy group, a C6-C12 aryl, a C5-C12 heterocyclic group, —NR3R4 (R3 is hydrogen, a C1-C20 alkyl group or a C6-C12 aryl, R4 is hydrogen, a C1-C20 alkyl group or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)₂R9 (R9 is a C6-C12 aryl or a C5-C12 heterocyclic group), or COR10 (R10 is a C1-C20 alkyl group, a C6-C12 aryl, a C3-C10 cycloalkyl group or a C5-C12 heterocyclic group), Re is hydrogen, CN, a C2-C20 alkyl group, a C2-C10 alkenyl group, a C1-C10 alkoxy, a C6-C12 aryl, a C5-C12 heterocyclic group, —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group) or —NHS(O)₂R9 (R9 is a C6-C12 aryl or a C5-C12 heterocyclic group), Rf and Rg are each hydrogen, and Rh is hydrogen, a C1-C5 alkyl group or a C2-C10 alkenyl group, the hetero atom of the heterocyclic group may be at least one selected from the group consisting of nitrogen, oxygen and sulfur, the alkyl group may be substituted with at least one substituent selected from the group consisting of OH, amine, a C6-C12 aryl, a C5-C10 heterocyclic group and a C3-C10 cycloalkyl group, the alkoxy group may be substituted with at least one substituent selected from the group consisting of halogen, a C6-C12 aryl, a C3-C10 cycloalkyl group, amine and an aminocarbonyl group, the heterocyclic group may be substituted with at least one substituent selected from the group consisting of an alkyl group, an amine-substituted alkyl group, amine, an amide group and a carboxyl group, the aryl may be substituted with at least one substituent selected from the group consisting of halogen, an alkyl group, a hydroxyl group, an alkoxy group, a carboxyl group, an ester group, a nitro group and an amine group, A, B, D, E, G, J, L and M may be linked with an adjacent group to form a fused ring, and Rd cannot be NO₂ when Rb is CH₃.

According to the present invention, stilbene derivatives are effective at inhibiting the function of cyclophilin, and are thus useful for the prevention of cyclophilin-related diseases, including viral infection diseases, such as hepatitis C virus (HCV), hepatitis B virus (HBV), human immunodeficiency virus (HIV), avian influenza (AI) virus and the like, cardiovascular diseases, rheumatoid arthritis, sepsis, asthma, periodontitis, aging, alopecia, neurodegenerative diseases, cancer, etc., or for the treatment of symptoms of such diseases. Moreover, the stilbene derivatives of the invention can be used in combination with existing therapeutic agents to thus increase the therapeutic effects.

DESCRIPTION OF THE SPECIFIC EMBODIMENTS

Hereinafter, a detailed description will be given of the present invention.

The present invention addresses a stilbene derivative represented by Chemical Formula 1 below. The stilbene derivative of the present invention has a structure appropriate for binding to an active pocket that is maintained in any protein having the function of cyclophilin and is thus useful as a cyclophilin inhibitor.

[Chemical Formula 1]

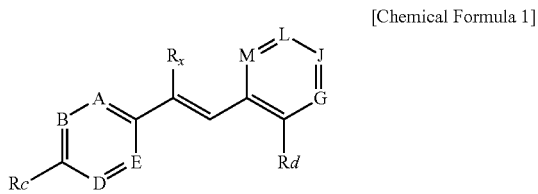

In Chemical Formula 1,
A is CRa or N,
B is CRb or N,
G is CRe or N
J is CRf or N,
M is CRg or N,
D, E, and L are CRh or N,
Rx is H, $CH_3$, CN, $NH_2$, F, Cl, Br or I,
wherein when Rx is H, $CH_3$, $NH_2$, F, Cl, Br or I,
Ra is hydrogen, $NO_2$, CN, OH, a C1-C5 alkyl group, a C2-C10 alkenyl group, a C1-C2 alkoxy group, —COOR1 (R1 is hydrogen or a C1-C5 alkyl group) or —OCOR2 (R2 is a C1-C5 alkyl group),
Rb is hydrogen, a C1-C20 alkyl group, a C2-C10 alkenyl group, a C1-C10 alkoxy group, —COOR1 (R1 is hydrogen or a C1-C5 alkyl group) or —OCOR2 (R2 is a C1-C5 alkyl group),
Rc is OH, $NO_2$, a C1-C20 alkyl group, a C3-C10 cycloalkyl group, a C2-C10 alkoxy group, a C6-C12 aryl, a C5-C12 heterocyclic group, —NR3R4 (R3 is hydrogen, a C1-C20 alkyl group or a C6-C12 aryl, R4 is hydrogen, a C1-C20 alkyl group or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)$_2$R9 (R9 is a C6-C12 aryl or a C5-C12 heterocyclic group), or —COR10 (R10 is a C1-C20 alkyl group, a C6-C12 aryl, a C3-C10 cycloalkyl group or a C5-C12 heterocyclic group),
Rd is halogen, $NO_2$, COOH, CN, a C2-C20 alkyl group, a C3-C10 cycloalkyl group, a C1-C10 alkoxy group, a C6-C12 aryl, a C5-C12 heterocyclic group, —NR3R4 (R3 is hydrogen, a C1-C20 alkyl or a C6-C12 aryl, R4 is hydrogen, a C1-C20 alkyl or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)$_2$R9 (R9 is a C6-C12 aryl or a C5-C12 heterocyclic group), or COR10 (R10 is a C1-C20 alkyl group, a C6-C12 aryl, a C3-C10 cycloalkyl group or a C5-C12 heterocyclic group), Re is hydrogen, $NH_2$, OH, CN, a C1-C20 alkyl group, a C2-C10 alkenyl group, a C1-C10 alkoxy, a C6-C12 aryl, a C5-C12 heterocyclic group, —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group) or —NHS(O)$_2$R9 (R9 is a C6-C12 aryl or a C5-C12 heterocyclic group),
Rf is hydrogen, $NH_2$, OH, $NO_2$, a C1-C4 alkyl group, a C2-C10 alkenyl group, a C1-C4 alkoxy group, a C6-C12 aryl, a C5-C12 heterocyclic group, —NHR11 (R11 is a C1-C2 alkyl group), —COOR12 (R12 is a C1-C2 alkyl group), —OCOR13 (R13 is a C1-C2 alkyl group), or —COR14 (R14 is a C1-C2 alkyl group),
Rg is hydrogen, $NH_2$, OH, halogen, $NO_2$, COOH, CN, a C1-C20 alkyl group, a C2-C10 alkenyl group, a C3-C10 cycloalkyl group, a C1-C10 alkoxy group, a C6-C12 aryl, a C5-C12 heterocyclic group, —NR3R4 (R3 is hydrogen, a C1-C20 alkyl or a C6-C12 aryl, R4 is hydrogen, a C1-C20 alkyl or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)$_2$R9 (R9 is a C6-C12 aryl or a C5-C12 heterocyclic group), or —COR10 (R10 is a C1-C20 alkyl group, a C6-C12 aryl, a C3-C10 cycloalkyl group or a C5-C12 heterocyclic group), and
Rh is hydrogen, $NH_2$, OH, a C1-C5 alkyl group or a C2-C10 alkenyl group,
when Rx is CN,
Ra is hydrogen,
Rb is hydrogen, a C1-C20 alkyl group, a C2-C10 alkenyl group, a C1-C10 alkoxy group, —COOR1 (R1 is hydrogen or a C1-C5 alkyl group) or —OCOR2 (R2 is a C1-C5 alkyl group),
Rc is OH, $NO_2$, a C1-C20 alkyl group, a C3-C10 cycloalkyl group, a C2-C10 alkoxy group, a C6-C12 aryl, a C5-C12 heterocyclic group, —NR3R4 (R3 is hydrogen, a C1-C20 alkyl group or a C6-C12 aryl, R4 is hydrogen, a C1-C20 alkyl group or a C6-C12 aryl, and R3 and R4 may be linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)$_2$R9 (R9 is a C6-C12 aryl or a C5-C12 heterocyclic group), or —COR10 (R10 is a C1-C20 alkyl group, a C6-C12 aryl, a C3-C10 cycloalkyl group, or a C5-C12 heterocyclic group),
Rd is hydrogen, halogen, $NO_2$, COOH, CN, a C2-C20 alkyl group, a C3-C10 cycloalkyl group, a C1-C10 alkoxy group, a C6-C12 aryl, a C5-C12 heterocyclic group, —NR3R4 (R3 is hydrogen, a C1-C20 alkyl group or a C6-C12 aryl, R4 is hydrogen, a C1-C20 alkyl group or a C6-C12 aryl, and R3 and R4 are linked to form a heterocycle, further containing at least one hetero atom), —COOR5 (R5 is a C1-C20 alkyl group, a C6-C12 aryl or a C3-C10 cycloalkyl group), —OCOR6 (R6 is a C1-C20 alkyl group, a C6-C12 aryl or a C3-C10 cycloalkyl group), —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group), —NHS(O)$_2$R9 (R9 is a C6-C12 aryl or a C5-C12 heterocyclic group), or COR10 (R10 is a C1-C20 alkyl group, a C6-C12 aryl, a C3-C10 cycloalkyl group or a C5-C12 heterocyclic group), Re is hydrogen, CN, a C2-C20 alkyl group, a C2-C10 alkenyl group, a C1-C10 alkoxy, a C6-C12 aryl, a C5-C12 heterocyclic group, —NR7CYR8 (Y is O or S, R7 is hydrogen or a C1-C5 alkyl group, and R8 is a C1-C20 alkyl group, a C6-C12 aryl, a C3-C10 cycloalkyl group or a C5-C12 heterocyclic group) or —NHS(O)$_2$R9 (R9 is a C6-C12 aryl or a C5-C12 heterocyclic group), Rf and Rg are each hydrogen, and Rh is hydrogen, a C1-C5 alkyl group or a C2-C10 alkenyl group, the hetero atom of the heterocyclic group may be at least one selected from the group consisting of nitrogen, oxygen and sulfur, the alkyl group may be substituted with at least one substituent selected from the group consisting of OH, amine, a C6-C12 aryl, a C5-C10 heterocyclic group and a C3-C10 cycloalkyl group, the alkoxy group may be substituted with at least one substituent selected from the group consisting of halogen, a C6-C12 aryl, a C3-C10 cycloalkyl group, amine and an aminocarbonyl group, the heterocyclic group may be substituted with at least one substituent selected from the group consisting of an alkyl group, an amine-substituted alkyl group, amine, an amide group and a carboxyl group, the aryl may be substituted with at least one substituent selected from the group consisting of halogen, an alkyl group, a hydroxyl group, an alkoxy group, a carboxyl group, an ester group, a nitro group and an amine group, A, B, D, E, G, J, L and M may be linked with an adjacent group to form a fused ring, and Rd cannot be NO$_2$ when Rb is CH$_3$.

The compound of the present invention may be synthesized via a variety of methods, and typically the synthesis process of the case where Rx of Chemical Formula 1 is CN may be different from those of the other cases.

When Rx is CN, the stilbene derivative represented by Chemical Formula 1 may be prepared by reacting a phenylacetonitrile derivative represented by Chemical Formula 2 below with a benzaldehyde derivative represented by Chemical Formula 3 below.

The phenylacetonitrile derivative represented by Chemical Formula 2 and the benzaldehyde derivative represented by Chemical Formula 3 may be commercially available products, or may be used after being prepared through methods known in the art.

The above reaction may be carried out in the presence of an organic solvent, or without any solvent. In this case, the reaction time may be reduced and the yield may be increased using microwaves.

The organic solvent is not limited, but preferably includes an alcohol, and more preferably butanol, methanol, ethanol, or propanol. A catalyst such as triphenylphosphine, piperidine or the like may be added to promote the reaction.

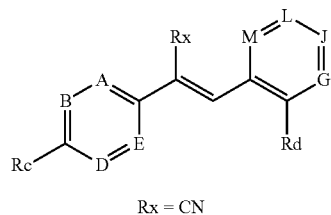

[Chemical Formula 1]

Rx = CN

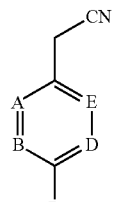

[Chemical Formula 2]

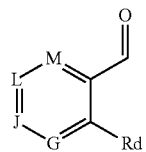

[Chemical Formula 3]

In Chemical Formulas 2 and 3,

A, B, D, E, G, J, L, M, Rc and Rd are as defined in A, B, D, E, G, J, L, M, Rc and Rd of Chemical Formula 1.

When Rx is H, CH$_3$, NH$_2$, F, Cl, Br or I, the stilbene derivative represented by Chemical Formula 1 may be prepared by reacting an olefin derivative represented by Chemical Formula 4 below with an organic halide derivative represented by Chemical Formula 5 below.

The olefin derivative represented by Chemical Formula 4 and the organic halide derivative represented by Chemical Formula 5 may be commercially available products, or may be used after being prepared through processes known in the art.

The above reaction is preferably carried out using a triethanolamine organic solvent in the presence of a palladium (II) acetate catalyst.

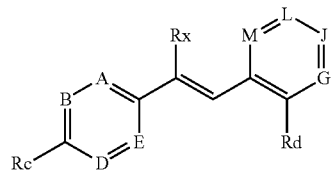

[Chemical Formula 1]

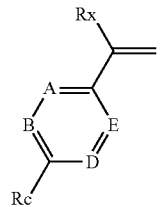

[Chemical Formula 4]

-continued

[Chemical Formula 5]

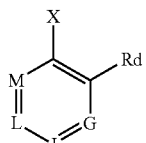

Rx = H, CH₃, NH₂, F, Cl, Br, I

In Chemical Formulas 4 and 5,

Rx is hydrogen, CH₃, NH₂, F, Cl, Br or I,

X is F, Cl, Br or I, and

A, B, D, E, G, J, L, M, Rc and Rd are as defined in A, B, D, E, G, J, L, M, Rc and Rd of Chemical Formula 1.

The stilbene derivative represented by Chemical Formula 1 according to the present invention may be used as a preventative or therapeutic agent of cyclophilin-related diseases along with a pharmaceutically acceptable carrier.

Also, the stilbene derivative represented by Chemical Formula 1 according to the present invention may be used as a reference material for comparison of efficacy of therapeutic agents for cyclophilin-related diseases.

In the present invention, the alkyl group or alkenyl group may be linear or branched.

As used herein, the term "halogen atom" may refer to fluorine, chlorine, bromine or iodine.

In the present invention, when A, B, D, E, G, J, L and M are linked with an adjacent group to form a fused ring, the fused ring is preferably a six-membered ring or a five-membered ring. Furthermore, the fused ring may contain at least one of hetero atoms such as N, O and S. The fused ring may be furan or thiophene.

In an embodiment of the present invention, A is preferably CRa or N, B is preferably CRb, G is preferably CRe, J is preferably CRf, M is preferably CRg or N, and D, E and L are preferably CH, but the present invention is not limited thereto.

In another embodiment of the present invention, Rb is preferably hydrogen or a C1-C8 alkyl group, but the present invention is not limited thereto.

In still another embodiment of the present invention, Rc is preferably a C1-C20 alkyl group, a C2-C10 alkoxy group, a phenylalkyl group, a nitro group, a C3-C10 cycloalkyl group, a C5-C12 heterocyclic group or a C1-C10 alkylketone, but the present invention is not limited thereto.

In yet another embodiment of the present invention, Rd is preferably a C2-C20 alkyl group; a C3-C10 ester group; a C3-C10 cycloalkyl group; a cycloalkyl-group-substituted methoxy; an amine-group-substituted ethoxy; a carboxyl group; a phenyl-group-substituted C2-C20 alkyl group, the phenyl group being unsubstituted or substituted with a C1-C5 alkyl group, a C1-C5 alkoxy group, a carboxyl group or an amine group; amine; N-methylpiperazine; piperidine; morpholine; or —COOR5 (R5 is a C1-C20 alkyl group, a C6-C12 aryl or a C3-C10 cycloalkyl group), but the present invention is not limited thereto.

In still yet another embodiment of the present invention, Re is preferably hydrogen, OH, a C1-C20 alkyl group, or a C1-C10 alkoxy group, but the present invention is not limited thereto.

In a further embodiment of the present invention, Rg is preferably hydrogen, OH, a C1-C20 alkyl group; a C3-C10 ester group; a C3-C10 cycloalkyl group; a cycloalkyl-group-substituted methoxy; an amine-group-substituted ethoxy; a phenyl-group-substituted C2-C20 alkyl group, the phenyl group being unsubstituted or substituted with a C1-C5 alkyl group, a C1-C5 alkoxy group, a carboxyl group or an amine group; amine; N-methylpiperazine; piperidine; morpholine; or a carboxyl group, but the present invention is not limited thereto.

In still a further embodiment of the present invention, Rh is preferably hydrogen, but the present invention is not limited thereto.

In the present invention, the alkyl group may be a substituted or unsubstituted alkyl, such as —CH₃, —CH₂CH₃, —CH₂CH₂CH₃, —CH₂(CH₂)₂CH₃, —CH₂(CH₂)₃CH₃, —CH(CH₃)CH₂CH₃, —CH₂CH(CH₃)CH₂CH₃, —CH₂CH₂CH(CH₃)₂, —CH(CH₃)₂, —C(CH₃)₃, —CH₂C(CH₃)₃, —CH₂CH(CH₃)₂, —CH(CH₃)CH(CH₃)₂, —CH(CH₃)C(CH₃)₃, —C(CH₃)₂CH₂CH₃, —C(CH₃)₂CH(CH₃)₂, —C(CH₃)₂C(CH₃)₃, —CH₂CH₂C(CH₃)₃, —CH₂CH(CH₃)CH(CH₃)₂, —CH₂CH₂C(CH₃)₂CH₂CH₃— CH₂CH₂CH(CH₃)CH₂C(CH₃)₃, —CH₂Ph, —CH₂CH₂Ph,

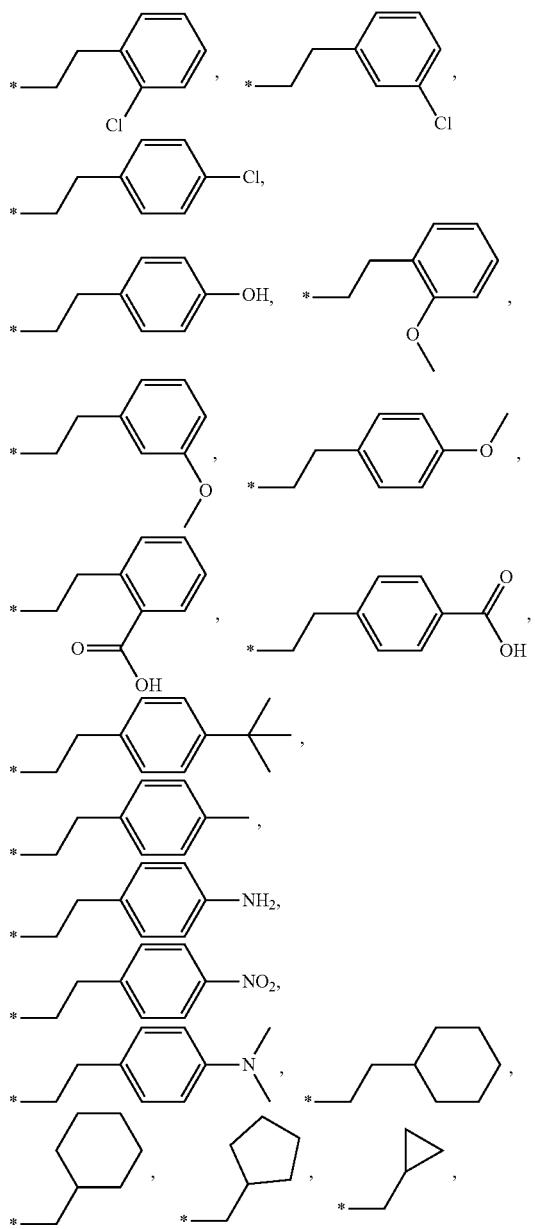

-continued

[structures]

but the present invention is not limited thereto.

In the present invention, the alkoxy group may be a substituted or unsubstituted alkoxy group, such as —OCH₃, —OCF₃, —OCH₂CH₃, —OCH₂CH₂CH₃, —OCH₂CH₂CH₂CH₃, —OCH(CH₃)CH₂CH₃, —OCH₂CONH₂, —OCH₂CH₂N(CH₃)₂,

[structures]

but the present invention is not limited thereto.

In the present invention, the heterocyclic group may be

[structures]

-continued

[structures]

but the present invention is not limited thereto.

In the present invention, the —NR3R4 may be —NH₂, —NHCH₃, —N(CH₃)₂,

[structures]

but the present invention is not limited thereto.

In the present invention, —COOR5 may be COOCH₃, —COOCH₂CH₃, COO(CH₂)₂CH₃, —COO(CH₂)₃CH₃, COO(CH₂)₄CH₃, COOCH(CH₃)₂,

[structures]

-continued

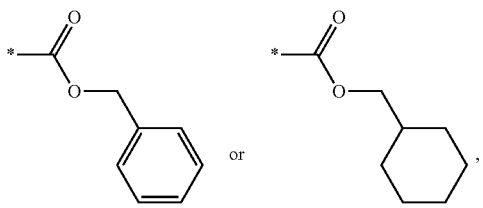

but the present invention is not limited thereto.

In the present invention, —OCOR6 may be

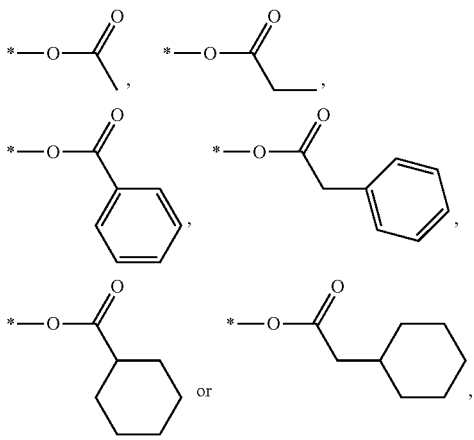

but the present invention is not limited thereto.

In the present invention, the —NR7CYR8 group may be

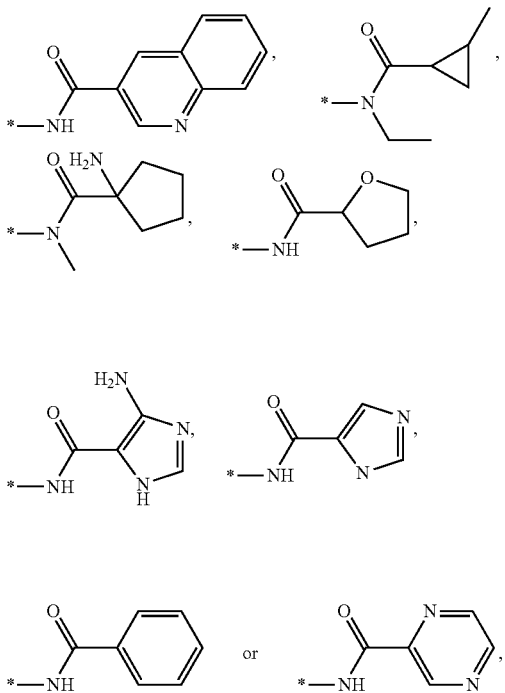

but the present invention is not limited thereto.

In the present invention, the —NHS(O)$_2$R9 group may be

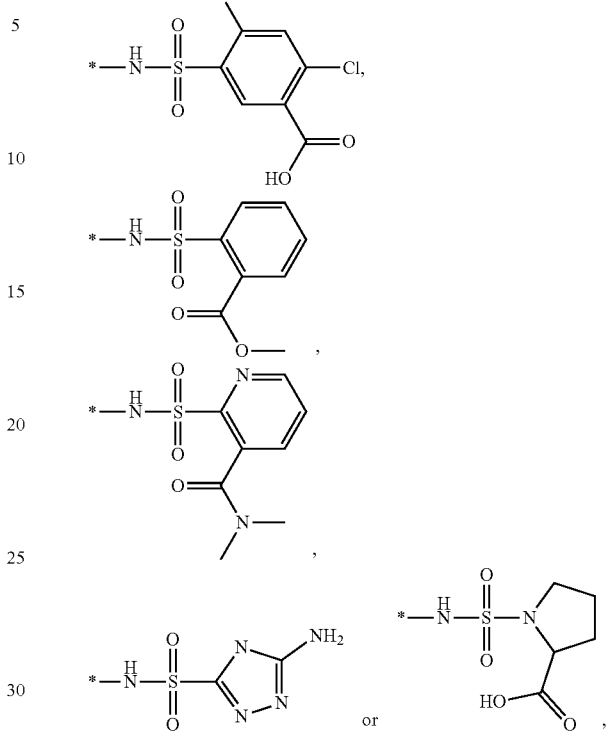

but the present invention is not limited thereto.

In the present invention, COR10 may be COC(CH$_3$)$_3$, but the present invention is not limited thereto.

As used herein, the term "pharmaceutically acceptable carrier" may be defined as a carrier or diluent that does not impair the biological activity or properties of the composition.

The pharmaceutically acceptable carrier or additive may include at least one of diluents or excipients such as a stabilizer, a filler, an extender, a wetting agent, a disintegrant, a lubricant, a binder, a surfactant, and the like, which are typically used.

The disintegrant may include agar, starch, alginic acid or a sodium salt thereof, anhydrous calcium hydrogen phosphate, and the like. The lubricant may include silica, talc, stearic acid or a magnesium salt or calcium salt thereof, polyethylene glycol, magnesium aluminometasilicate, and the like. The binder may include magnesium aluminum silicate, starch paste, gelatin, tragacanth, methylcellulose, sodium carboxymethylcellulose, polyvinylpyrrolidone, low-substituted hydroxypropylcellulose, and the like.

In addition thereto, lactose, dextrose, sucrose, mannitol, sorbitol, cellulose or glycine may be used as the diluent. In some cases, commonly known boiling salts, absorbents, coloring agents, flavoring agents, sweetening agents and the like may be used therewith.

Also, the stabilizer may include a sodium (Na)-free stabilizer, examples of which include magnesium aluminometasilicate, magnesium aluminosilicate, magnesium aluminate, dried aluminum hydroxide, synthetic hydrotalcite, synthetic aluminum silicate, magnesium carbonate, precipitated calcium carbonate, magnesium oxide, aluminum hydroxide, L-arginine, potassium phosphate, dipotassium hydrogen phosphate, potassium dihydrogen phosphate, ammonium chloride, aluminum chloride, and the like, which may be used alone or in combinations of two or more thereof.

A pharmaceutical composition, containing the stilbene derivative of Chemical Formula 1 of the present invention, may be administered in a variety of ways that facilitate administration of the compound into the organism. The pharmaceutical composition containing the compound of the present invention may be administered via oral administration, intrarectal administration, intravaginal administration, intranasal administration, intraocular administration, intraoral administration, sublingual administration, subcutaneous administration, intramuscular administration, intravenous administration, intrathecal administration, intradermal administration, epidural administration, and the like.

The pharmaceutical composition, containing the compound of the present invention, may be provided in a dosage form of a tablet, capsule, powder, dropping pill, pulvis, bolus, tincture or cataplasm. The preferred tablet may be a typical tablet, coated tablet, dispersible tablet, effervescent tablet, etc., or may be a multi-compressed tablet, such as a double tablet, a tablet-in-tablet, a multilayer tablet, etc.

The preferred administration amount of the stilbene derivative or pharmaceutically acceptable salt thereof included in the pharmaceutical composition containing the compound of the present invention varies depending on the status and body weight of a patient, the severity of disease, the type of drug, the administration route and duration, but may be appropriately selected by those skilled in the art.

A better understanding of the present invention may be achieved via the following non-limiting examples, which are merely set forth to illustrate but are not to be construed as limiting the scope of the present invention. The following examples may be appropriately modified and altered within the scope of the present invention.

Example 1. Preparation of Stilbene Derivative in which Rx is CN

1) Use of Solvent 1 eq. of a phenylacetonitrile derivative of Chemical Formula 2 and 1.3 eq. of a benzaldehyde derivative of Chemical Formula 3 were refluxed with 0.2 eq. of triphenylphosphine in a butanol solvent, followed by a Knoevenagel condensation reaction, thus yielding a compound of Chemical Formula 1.

2) Use of Microwaves 1 eq. of a phenylacetonitrile derivative of Chemical Formula 2, 1.3 eq. of a benzaldehyde derivative of Chemical Formula 3 and 0.2 eq. of triphenylphosphine were treated with microwaves, thus yielding a compound of Chemical Formula 1. When the microwaves are used, the reaction time may be shortened and the yield may be increased.

[Scheme 1]

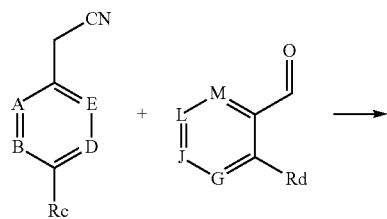

-continued

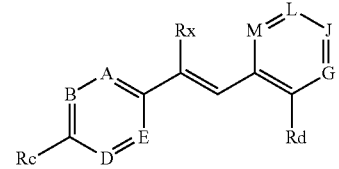

Rx = CN

[Chemical Formula 2] [Chemical Formula 3] [Chemical Formula 1]

Example 2. Preparation of Derivative in which Rx is Hydrogen, $CH_3$, $NH_2$, F, Cl, Br, I 1 eq. of an olefin derivative of Chemical Formula 4 and 1 eq. of an organic halide derivative of Chemical Formula 5 were refluxed with 0.01 eq. of palladium (II) acetate in a triethanolamine solvent, followed by a Heck olefination reaction, thus yielding a compound of Chemical Formula 1.

[Scheme 2]

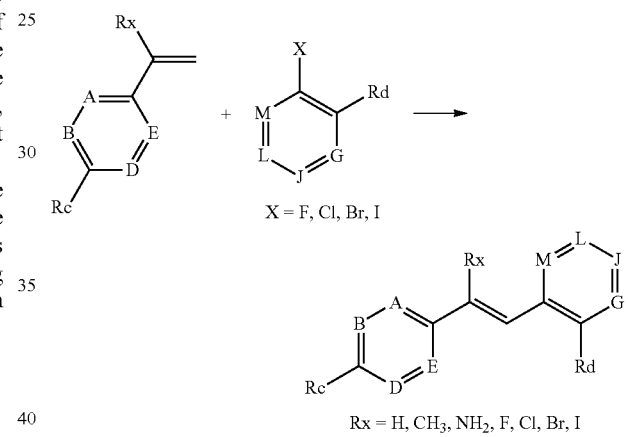

Rx = H, $CH_3$, $NH_2$, F, Cl, Br, I

[Chemical Formula 4] [Chemical Formula 5] [Chemical Formula 1]

Test Example 1. Evaluation of Cis-Trans Isomerase Inhibitory Activity of Stilbene Derivative Chymotrypsin cleaves a trans-type alanine-proline peptide bond. When Suc-AAPF-pNA (a peptide substrate) and chymotrypsin are mixed, the trans-type peptide substrate is cleaved and the cis-type peptide substrate remains. The remaining cis-type peptide substrate is converted into a trans form by a cis-trans isomerase and is then cleaved again by chymotrypsin. When the cis-trans isomerase is present, chymotrypsin is able to cleave a larger amount of trans-type peptide substrate within a predetermined period of time, from which the activity of the cis-trans isomerase may be determined. The amount of the cleaved trans-type peptide substrate is measured using absorbance at 390 nm.

Cyclophilin has cis-trans isomerase activity, and accelerates the cleavage of trans-type peptide substrate by chymotrypsin. When the stilbene derivatives of the present invention were treated together with cyclophilin, the cleavage of the peptide substrate by chymotrypsin was not observed to accelerate. Thereby, the stilbene derivatives of the invention can be concluded to inhibit the activity of cyclophilin.

Compounds 1 to 155 (Tables 1 to 10) below may be grouped as follows based on the cis-trans isomerase inhibitory activity ($IC_{50}$) values:

Group A ($G_A$): $IC_{50}$ of 2000 nM or less but exceeding 200 nM,

Group B ($G_B$): $IC_{50}$ of 200 nM or less but exceeding 20 nM, and

Group C ($G_C$): $IC_{50}$ of 20 nM or less.

TABLE 1

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 1 | CN | H | H | $CH_3$ | $N(CH_3)_2$ | H | H | $G_A$ | $G_D$ | $G_G$ |
| 2 | CN | H | H | $CH_2CH_3$ | COOH | H | H | $G_A$ | $G_D$ | $G_G$ |
| 3 | CN | H | H | $CH_2CH_3$ | $N(CH_3)_2$ | H | H | $G_A$ | $G_D$ | $G_G$ |
| 4 | CN | H | H | i-Pr | Cl | H | H | $G_A$ | $G_D$ | $G_G$ |
| 5 | CN | H | H | i-Pr | COOH | H | H | $G_A$ | $G_D$ | $G_G$ |
| 6 | CN | H | H | i-Pr | $OCH_3$ | H | H | $G_A$ | $G_D$ | $G_G$ |
| 7 | CN | H | H | $NO_2$ | $N(CH_3)_2$ | H | H | $G_A$ | $G_D$ | $G_G$ |
| 8 | CN | H | H | $CH_2CH_2CH_2CH_3$ | COOH | H | H | $G_B$ | $G_E$ | $G_H$ |
| 9 | CN | H | H | $CH(CH_3)CH_2CH_3$ | COOH | H | H | $G_B$ | $G_E$ | $G_H$ |
| 10 | CN | H | H | t-Bu | COOH | H | H | $G_B$ | $G_E$ | $G_H$ |
| 11 | CN | H | H | t-Bu | $OCH_3$ | H | H | $G_A$ | $G_D$ | $G_G$ |
| 12 | CN | H | $CH_3$ | $CH_3$ | $OCH_3$ | H | H | $G_A$ | $G_D$ | $G_G$ |
| 13 | CN | H | $CH_3$ | $CH_3$ | COOH | H | H | $G_A$ | $G_D$ | $G_G$ |
| 14 | CN | H | H | $COC(CH_3)_3$ | $OCH_3$ | H | H | $G_B$ | $G_E$ | $G_H$ |
| 15 | CN | H | H | $COC(CH_3)_3$ | COOH | H | H | $G_A$ | $G_D$ | $G_G$ |
| 16 | CN | H | H | $OCH_2CH_3$ | $OCH_3$ | H | H | $G_A$ | $G_D$ | $G_G$ |
| 17 | CN | H | H | $OCH_2CH_3$ | COOH | H | H | $G_A$ | $G_D$ | $G_G$ |
| 18 | CN | H | H | $OCH_2CH_2CH_2CH_3$ | $OCH_3$ | H | H | $G_B$ | $G_E$ | $G_H$ |
| 19 | CN | H | H | $OCH_2CH_2CH_2CH_3$ | COOH | H | H | $G_B$ | $G_E$ | $G_H$ |
| 20 | CN | H | H | $CH_2Ph$ | $OCH_3$ | H | H | $G_C$ | $G_F$ | $G_I$ |
| 21 | CN | H | H | $CH_2Ph$ | COOH | H | H | $G_C$ | $G_F$ | $G_I$ |
| 22 | CN | H | H | $NO_2$ | $CH_2CH_3$ | H | H | $G_A$ | $G_D$ | $G_G$ |
| 23 | CN | H | H | $NO_2$ | i-Pr | H | H | $G_A$ | $G_D$ | $G_G$ |
| 24 | CN | H | H | $NO_2$ | $NH_2$ | H | H | $G_A$ | $G_D$ | $G_G$ |
| 25 | CN | H | H | $NO_2$ | *—N(piperazinyl)N— | H | H | $G_A$ | $G_D$ | $G_G$ |
| 26 | CN | H | H | $NO_2$ | $OCH(CH_3)CH_2CH_3$ | H | H | $G_A$ | $G_D$ | $G_G$ |
| 27 | CN | H | H | $NO_2$ | *—O—cyclopropylmethyl | H | H | $G_B$ | $G_E$ | $G_H$ |
| 28 | CN | H | H | $NO_2$ | $OCH_2CH_2N(CH_3)_2$ | H | H | $G_A$ | $G_D$ | $G_G$ |
| 29 | CN | H | H | $NO_2$ | *—N(piperidinyl) | H | H | $G_A$ | $G_D$ | $G_G$ |
| 30 | CN | H | H | $NO_2$ | *—N(morpholinyl)O | H | H | $G_A$ | $G_D$ | $G_G$ |
| 31 | CN | H | H | $NO_2$ | *—cyclohexyl | H | H | $G_B$ | $G_E$ | $G_H$ |
| 32 | CN | H | H | $NO_2$ | H | $OCH_2CH_2CH(CH_3)_2$ | H | $G_A$ | $G_D$ | $G_G$ |
| 33 | CN | H | H | $NO_2$ | H | $OCH_2CH_2CH_2N(CH_3)_2$ | H | $G_A$ | $G_D$ | $G_G$ |
| 34 | CN | H | H | $NO_2$ | $CH_2CH(CH_3)_2$ | H | H | $G_A$ | $G_D$ | $G_G$ |
| 35 | CN | H | H | $NO_2$ | $CH_2C(CH_3)_3$ | H | H | $G_B$ | $G_E$ | $G_H$ |
| 36 | CN | H | H | $NO_2$ | $CH_2CH_2CH(CH_3)_2$ | H | H | $G_B$ | $G_E$ | $G_H$ |

TABLE 1-continued

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 37 | CN | H | H | NO$_2$ | 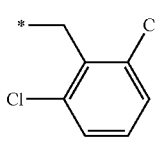 | H | H | G$_B$ | G$_E$ | G$_H$ |
| 38 | CN | H | H | NO$_2$ | CH$_2$CH$_2$Ph | H | H | G$_B$ | G$_E$ | G$_H$ |
| 39 | CN | H | H | NO$_2$ | 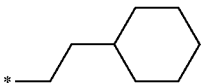 | H | H | G$_C$ | G$_F$ | G$_I$ |
| 40 | CN | H | H | NO$_2$ | 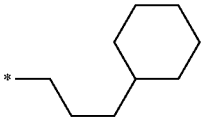 | H | H | G$_C$ | G$_F$ | G$_I$ |
| 41 | CN | H | H | NO$_2$ | 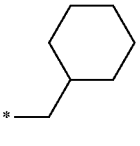 | H | H | G$_C$ | G$_F$ | G$_I$ |
| 42 | CN | H | H | NO$_2$ | CH$_2$CH$_2$CH$_2$Ph | H | H | G$_A$ | G$_D$ | G$_G$ |
| 43 | CN | H | H | NO$_2$ | CH$_2$CH$_2$C(CH$_3$)$_3$ | H | H | G$_B$ | G$_E$ | G$_H$ |
| 44 | CN | H | H | NO$_2$ | 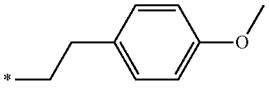 | H | H | G$_B$ | G$_E$ | G$_H$ |
| 45 | CN | H | H | NO$_2$ | 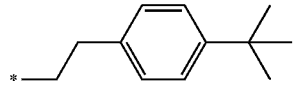 | H | H | G$_B$ | G$_E$ | G$_H$ |
| 46 | CN | H | H | NO$_2$ | 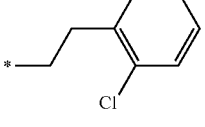 | H | H | G$_B$ | G$_E$ | G$_H$ |
| 47 | CN | H | H | NO$_2$ | 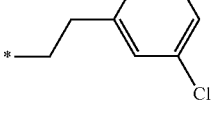 | H | H | G$_B$ | G$_E$ | G$_H$ |
| 48 | CN | H | H | NO$_2$ | 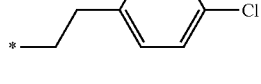 | H | H | G$_B$ | G$_E$ | G$_H$ |
| 49 | CN | H | H | NO$_2$ | 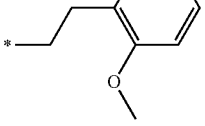 | H | H | G$_A$ | G$_D$ | G$_G$ |

TABLE 1-continued

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 51 | CN | H | H | NO₂ | *-CH₂CH₂-C₆H₄-COOH (para) | H | H | G_A | G_D | G_G |
| 52 | CN | H | H | NO₂ | *-CH₂CH₂-C₆H₄-CH₃ (para) | H | H | G_B | G_E | G_H |
| 53 | CN | H | H | NO₂ | *-CH₂CH₂-C₆H₄-NH₂ (para) | H | H | G_B | G_E | G_H |
| 54 | CN | H | H | CH₂C(CH₃)₃ | COOH | H | H | G_C | G_F | G_I |
| 55 | CN | H | H | *-CH(CH(CH₃)₂)CH₃ | COOH | H | H | G_B | G_E | G_H |
| 56 | CN | H | H | *-CH(CH₃)C(CH₃)₃ | COOH | H | H | G_B | G_E | G_H |
| 57 | CN | H | H | *-CH₂CH₂C(CH₃)₃ | COOH | H | H | G_C | G_F | G_I |
| 58 | CN | H | H | *-CH₂CH(CH₃)CH(CH₃)₂ | COOH | H | H | G_B | G_E | G_H |
| 59 | CN | H | H | *-CH₂-cyclohexyl | COOH | H | H | G_C | G_F | G_I |
| 60 | CN | H | H | *-CH₂CH₂-cyclohexyl | COOH | H | H | G_C | G_F | G_I |
| 61 | CN | H | H | *-CH₂-cyclopropyl | COOH | H | H | G_C | G_F | G_I |
| 62 | CN | H | H | *-CH₂CH₂-cyclopropyl | COOH | H | H | G_C | G_F | G_I |

TABLE 1-continued

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 63 | CN | H | H | *CH$_2$C(CH$_3$)$_2$CH$_2$-cyclopropyl | COOH | H | H | $G_B$ | $G_E$ | $G_H$ |
| 64 | H | H | H | CH$_2$C(CH$_3$)$_3$ | COO(CH$_2$)$_3$CH$_3$ | H | H | $G_C$ | $G_F$ | $G_I$ |
| 65 | H | H | H | CH$_2$C(CH$_3$)$_3$ | COO(CH$_2$)$_3$CH$_3$ | CH$_3$ | H | $G_B$ | $G_E$ | $G_H$ |
| 66 | H | H | H | CH$_2$C(CH$_3$)$_3$ | COO(CH$_2$)$_3$CH$_3$ | CH$_2$CH$_3$ | H | $G_B$ | $G_E$ | $G_H$ |
| 67 | H | CH$_3$ | H | CH$_2$C(CH$_3$)$_3$ | COO(CH$_2$)$_3$CH$_3$ | H | H | $G_B$ | $G_E$ | $G_H$ |
| 68 | H | CH$_2$CH$_3$ | H | CH$_2$C(CH$_3$)$_3$ | COO(CH$_2$)$_3$CH$_3$ | H | H | $G_B$ | $G_E$ | $G_H$ |
| 69 | H | H | H | CH$_2$C(CH$_3$)$_3$ | COO(CH$_2$)$_3$CH$_3$ | H | CH$_3$ | $G_B$ | $G_E$ | $G_H$ |
| 70 | H | H | H | CH$_2$C(CH$_3$)$_3$ | COO(CH$_2$)$_3$CH$_3$ | CH$_3$ | CH$_3$ | $G_B$ | $G_E$ | $G_H$ |
| 71 | H | H | H | CH$_2$C(CH$_3$)$_3$ | COO(CH$_2$)$_2$CH$_3$ | H | H | $G_C$ | $G_F$ | $G_I$ |
| 72 | H | H | H | CH$_2$C(CH$_3$)$_3$ | COO(CH$_2$)$_4$CH$_3$ | H | H | $G_C$ | $G_F$ | $G_I$ |
| 73 | H | H | H | CH$_2$C(CH$_3$)$_3$ | COOCH(CH$_3$)$_2$ | H | H | $G_C$ | $G_F$ | $G_I$ |
| 74 | H | H | H | CH$_2$C(CH$_3$)$_3$ | *C(=O)OCH$_2$-cyclohexyl | H | H | $G_C$ | $G_F$ | $G_I$ |
| 75 | H | H | H | CH$_2$C(CH$_3$)$_3$ | *C(=O)OCH$_2$-(piperidin-2-yl) | H | H | $G_B$ | $G_E$ | $G_H$ |
| 76 | H | H | H | CH$_2$C(CH$_3$)$_3$ | COOCH$_2$Ph | H | H | $G_C$ | $G_F$ | $G_I$ |
| 77 | H | H | H | CH$_2$C(CH$_3$)$_3$ | *C(=O)O-cyclohexyl | H | H | $G_B$ | $G_E$ | $G_H$ |
| 78 | H | H | H | CH$_2$CH(CH$_3$)CH$_2$CH$_3$ | COO(CH$_2$)$_3$CH$_3$ | H | H | $G_B$ | $G_E$ | $G_H$ |
| 79 | H | H | H | *CH$_2$-cyclopentyl | COO(CH$_2$)$_3$CH$_3$ | H | H | $G_B$ | $G_E$ | $G_H$ |
| 80 | H | H | H | *CH$_2$-cyclohexyl | COO(CH$_2$)$_3$CH$_3$ | H | H | $G_B$ | $G_E$ | $G_H$ |
| 81 | H | H | H | *CH$_2$-phenyl | COO(CH$_2$)$_3$CH$_3$ | H | H | $G_B$ | $G_E$ | $G_H$ |
| 82 | CH$_3$ | H | H | CH$_2$C(CH$_3$)$_3$ | COO(CH$_2$)$_3$CH$_3$ | H | H | $G_B$ | $G_E$ | $G_H$ |
| 83 | CH$_3$ | H | H | CH$_2$C(CH$_3$)$_3$ | COO(CH$_2$)$_3$CH$_3$ | CH$_3$ | H | $G_B$ | $G_E$ | $G_H$ |
| 84 | CH$_3$ | CH$_3$ | H | CH$_2$C(CH$_3$)$_3$ | COO(CH$_2$)$_3$CH$_3$ | H | H | $G_B$ | $G_E$ | $G_H$ |

TABLE 1-continued

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 85 | CH$_3$ | H | H | CH$_2$C(CH$_3$)$_3$ | COO(CH$_2$)$_3$CH$_3$ | H | CH$_3$ | G$_B$ | G$_E$ | G$_H$ |
| 86 | CH$_3$ | H | H | CH$_2$C(CH$_3$)$_3$ | COO(CH$_2$)$_3$CH$_3$ | CH$_3$ | CH$_3$ | G$_B$ | G$_E$ | G$_H$ |
| 87 | CH$_3$ | H | H | CH$_2$C(CH$_3$)$_3$ | COO(CH$_2$)$_2$CH$_3$ | H | H | G$_B$ | G$_E$ | G$_H$ |
| 88 | CH$_3$ | H | H | CH$_2$C(CH$_3$)$_3$ | COO(CH$_2$)$_4$CH$_3$ | H | H | G$_B$ | G$_E$ | G$_H$ |
| 89 | CH$_3$ | H | H | CH$_2$C(CH$_3$)$_3$ | COOCH(CH$_3$)$_2$ | H | H | G$_B$ | G$_E$ | G$_H$ |
| 90 | CH$_3$ | H | H | CH$_2$C(CH$_3$)$_3$ | 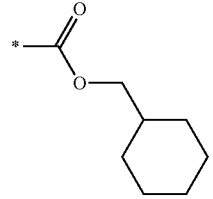 | H | H | G$_B$ | G$_E$ | G$_H$ |
| 91 | CH$_3$ | H | H | CH$_2$C(CH$_3$)$_3$ | 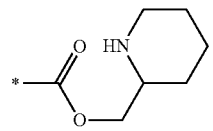 | H | H | G$_B$ | G$_E$ | G$_H$ |
| 92 | CH$_3$ | H | H | CH$_2$C(CH$_3$)$_3$ | COOCH$_2$Ph | H | H | G$_B$ | G$_E$ | G$_H$ |
| 93 | CH$_3$ | H | H | CH$_2$C(CH$_3$)$_3$ | 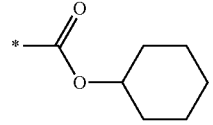 | H | H | G$_B$ | G$_E$ | G$_H$ |
| 94 | CH$_3$ | H | H | CH$_2$CH(CH$_3$)CH$_2$CH$_3$ | COO(CH$_2$)$_3$CH$_3$ | H | H | G$_B$ | G$_E$ | G$_H$ |
| 95 | CH$_3$ | H | H | 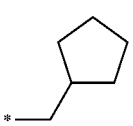 | COO(CH$_2$)$_3$CH$_3$ | H | H | G$_B$ | G$_E$ | G$_H$ |
| 96 | CH$_3$ | H | H | 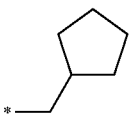 | COO(CH$_2$)$_3$CH$_3$ | H | H | G$_B$ | G$_E$ | G$_H$ |
| 97 | CH$_3$ | H | H | 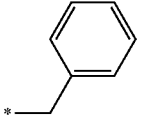 | COO(CH$_2$)$_3$CH$_3$ | H | H | G$_B$ | G$_E$ | G$_H$ |
| 98 | NH$_2$ | H | H | CH$_2$C(CH$_3$)$_3$ | COO(CH$_2$)$_3$CH$_3$ | H | H | G$_B$ | G$_E$ | G$_H$ |
| 99 | NH$_2$ | H | H | CH$_2$C(CH$_3$)$_3$ | COO(CH$_2$)$_3$CH$_3$ | CH$_3$ | H | G$_B$ | G$_E$ | G$_H$ |
| 100 | NH$_2$ | CH$_3$ | H | CH$_2$C(CH$_3$)$_3$ | COO(CH$_2$)$_3$CH$_3$ | H | H | G$_B$ | G$_E$ | G$_H$ |
| 101 | NH$_2$ | H | H | CH$_2$C(CH$_3$)$_3$ | COO(CH$_2$)$_3$CH$_3$ | H | CH$_3$ | G$_B$ | G$_E$ | G$_H$ |
| 102 | NH$_2$ | H | H | CH$_2$C(CH$_3$)$_3$ | COO(CH$_2$)$_3$CH$_3$ | CH$_3$ | CH$_3$ | G$_B$ | G$_E$ | G$_H$ |
| 103 | NH$_2$ | H | H | CH$_2$C(CH$_3$)$_3$ | COO(CH$_2$)$_4$CH$_3$ | H | H | G$_B$ | G$_E$ | G$_H$ |
| 104 | NH$_2$ | H | H | CH$_2$C(CH$_3$)$_3$ | COOCH(CH$_3$)$_2$ | H | H | G$_B$ | G$_E$ | G$_H$ |

TABLE 1-continued

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 105 | $NH_2$ | H | H | $CH_2C(CH_3)_3$ | 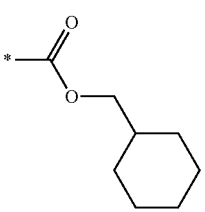 | H | H | $G_B$ | $G_E$ | $G_H$ |
| 106 | $NH_2$ | H | H | $CH_2C(CH_3)_3$ | $COOCH_2Ph$ | H | H | $G_B$ | $G_E$ | $G_H$ |
| 107 | $NH_2$ | H | H | $CH_2C(CH_3)_3$ | 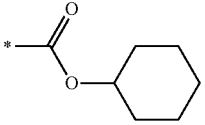 | H | H | $G_B$ | $G_E$ | $G_H$ |
| 108 | $NH_2$ | H | H | $CH_2CH(CH_3)CH_2CH_3$ | $COO(CH_2)_3CH_3$ | H | H | $G_B$ | $G_E$ | $G_H$ |
| 109 | $NH_2$ | H | H | 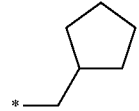 | $COO(CH_2)_3CH_3$ | H | H | $G_B$ | $G_E$ | $G_H$ |
| 110 | $NH_2$ | H | H | 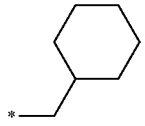 | $COO(CH_2)_3CH_3$ | H | H | $G_B$ | $G_E$ | $G_H$ |
| 111 | $NH_2$ | H | H | 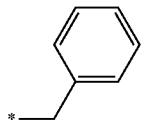 | $COO(CH_2)_3CH_3$ | H | H | $G_B$ | $G_E$ | $G_H$ |
| 112 | F | H | H | $CH_2C(CH_3)_3$ | $COO(CH_2)_3CH_3$ | H | H | $G_C$ | $G_F$ | $G_I$ |
| 113 | Cl | H | H | $CH_2C(CH_3)_3$ | $COO(CH_2)_3CH_3$ | $CH_3$ | H | $G_C$ | $G_F$ | $G_I$ |
| 114 | Br | $CH_3$ | H | $CH_2C(CH_3)_3$ | $COO(CH_2)_3CH_3$ | H | H | $G_C$ | $G_F$ | $G_I$ |
| 115 | I | H | H | $CH_2C(CH_3)_3$ | $COO(CH_2)_3CH_3$ | H | $CH_3$ | $G_C$ | $G_F$ | $G_I$ |
| 116 | F | H | H | $CH_2C(CH_3)_3$ | $COO(CH_2)_3CH_3$ | $CH_3$ | $CH_3$ | $G_C$ | $G_F$ | $G_I$ |
| 117 | Cl | H | H | $CH_2C(CH_3)_3$ | $COO(CH_2)_4CH_3$ | H | H | $G_C$ | $G_F$ | $G_I$ |
| 118 | Br | H | H | $CH_2C(CH_3)_3$ | $COOCH(CH_3)_2$ | H | H | $G_C$ | $G_F$ | $G_I$ |
| 119 | I | H | H | $CH_2C(CH_3)_3$ | 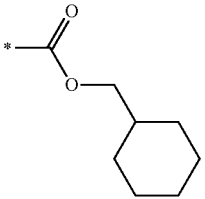 | H | H | $G_C$ | $G_F$ | $G_I$ |
| 120 | F | H | H | $CH_2C(CH_3)_3$ | $COOCH_2Ph$ | H | H | $G_C$ | $G_F$ | $G_{I'}$ |
| 121 | Cl | H | H | $CH_2C(CH_3)_3$ | 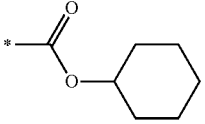 | H | H | $G_C$ | $G_F$ | $G_I$ |

TABLE 1-continued

A=CRa, B=CRb, G=CRe, J=CRf, D=E=L=M=CH

| Compound | Rx | Ra | Rb | Rc | Rd | Re | Rf | Test Example 1 | 3 | 4 |
|---|---|---|---|---|---|---|---|---|---|---|
| 122 | Br | H | H | $CH_2CH(CH_3)CH_2CH_3$ | $COO(CH_2)_3CH_3$ | H | H | $G_B$ | $G_E$ | $G_H$ |
| 123 | I | H | H | benzyl (–CH$_2$–C$_6$H$_5$) | $COO(CH_2)_3CH_3$ | H | H | $G_B$ | $G_E$ | $G_H$ |
| 124 | H | H | H | $CH_2C(CH_3)_3$ | $COOCH_3$ | H | H | $G_C$ | $G_F$ | $G_I$ |
| 125 | H | H | H | $CH_2CH(CH_3)CH_2CH_3$ | $COOCH_3$ | H | H | $G_B$ | $G_E$ | $G_H$ |
| 126 | H | H | H | cyclopentylmethyl | $COOCH_3$ | H | H | $G_B$ | $G_E$ | $G_H$ |
| 127 | H | H | H | cyclohexylmethyl | $COOCH_3$ | H | H | $G_B$ | $G_E$ | $G_H$ |
| 128 | H | H | H | benzyl (–CH$_2$–C$_6$H$_5$) | $COOCH_3$ | H | H | $G_B$ | $G_E$ | $G_H$ |
| 129 | H | H | H | isobutyl (–CH$_2$CH(CH$_3$)$_2$) | $COOCH_3$ | H | H | $G_B$ | $G_E$ | $G_H$ |
| 130 | H | H | H | $CH_2(CH_2)_3CH_3$ | $COOCH_3$ | H | H | $G_C$ | $G_F$ | $G_I$ |
| 131 | H | H | H | isobutyl (–CH$_2$CH(CH$_3$)$_2$) | $COO(CH_2)_3CH_3$ | H | H | $G_C$ | $G_F$ | $G_I$ |
| 132 | H | H | H | $CH_2(CH_2)_3CH_3$ | $COO(CH_2)_3CH_3$ | H | H | $G_C$ | $G_F$ | $G_I$ |
| 133 | H | H | H | $CH_2C(CH_3)_3$ | pyrrolidin-1-ylcarbonyl (–C(=O)–N(pyrrolidine)) | H | H | $G_B$ | $G_E$ | $G_H$ |
| 134 | H | H | H | $CH_2C(CH_3)_3$ | COOH | H | H | $G_C$ | $G_F$ | $G_I$ |
| 135 | H | H | H | $CH_2C(CH_3)_3$ | COOH | OH | H | $G_C$ | $G_F$ | $G_I$ |
| 136 | H | H | H | $CH_2C(CH_3)_3$ | COOH | H | OH | $G_C$ | $G_F$ | $G_I$ |
| 137 | H | H | H | $CH_2C(CH_3)_3$ | COOH | $NH_2$ | H | $G_C$ | $G_F$ | $G_I$ |
| 138 | H | H | H | $CH_2C(CH_3)_3$ | COOH | H | $NH_2$ | $G_C$ | $G_F$ | $G_I$ |
| 139 | H | H | H | $CH_2C(CH_3)_3$ | COOH | $CH_3$ | H | $G_C$ | $G_F$ | $G_I$ |
| 140 | H | H | H | $CH_2C(CH_3)_3$ | COOH | H | $CH_3$ | $G_C$ | $G_F$ | $G_I$ |
| 141 | H | H | H | $CH_2C(CH_3)_3$ | $CONH_2$ | H | H | $G_C$ | $G_F$ | $G_I$ |

TABLE 2

A=CRa, B=CRb, G=CRe D=E=M=CH

| Compound | $R_x$ | $R_a$ | $R_b$ | $R_c$ | $R_d$ | $R_e$ | J and L | Fused ring formation of Test Example 1 | 3 | 4 |
|---|---|---|---|---|---|---|---|---|---|---|
| 142 | H | H | H | $CH_2C(CH_3)_3$ | $COO(CH_2)_3CH_3$ | H | 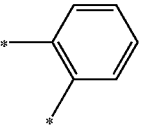 | $G_B$ | $G_E$ | $G_H$ |

TABLE 3

A = N, B = CRb, G = CRe, J = CRf, D = E = L = M = CH

| Compound | $R_x$ | $R_b$ | $R_c$ | $R_d$ | $R_e$ | $R_f$ | Test Example 1 | 3 | 4 |
|---|---|---|---|---|---|---|---|---|---|
| 143 | H | H | H | $CH_2C(CH_3)_3$ | $COO(CH_2)_3CH_3$ | H | $G_B$ | $G_E$ | $G_H$ |

TABLE 4

A = CRa, B = N, G = CRe, J = CRf, D = E = L = M = CH

| Compound | $R_x$ | $R_a$ | $R_c$ | $R_d$ | $R_e$ | $R_f$ | Test Example 1 | 3 | 4 |
|---|---|---|---|---|---|---|---|---|---|
| 144 | H | H | H | $CH_2C(CH_3)_3$ | $COO(CH_2)_3CH_3$ | H | $G_B$ | $G_E$ | $G_H$ |

TABLE 5

A = CRa, B = CRb, G = N, J = CRf, D = E = L = M = CH

| Compound | $R_x$ | $R_a$ | $R_b$ | $R_c$ | $R_d$ | $R_f$ | Test Example 1 | 3 | 4 |
|---|---|---|---|---|---|---|---|---|---|
| 145 | H | H | H | H | $CH_2C(CH_3)_3$ | $COO(CH_2)_3CH_3$ | H | $G_B$ | $G_E$ | $G_H$ |

TABLE 6

A = CRa, B = CRb, G = CRe, J = N, D = E = L = M = CH

| Compound | $R_x$ | $R_a$ | $R_b$ | $R_c$ | $R_d$ | $R_e$ | Test Example 1 | 3 | 4 |
|---|---|---|---|---|---|---|---|---|---|
| 146 | H | H | H | H | $CH_2C(CH_3)_3$ | $COO(CH_2)_3CH_3$ | H | $G_B$ | $G_E$ | $G_H$ |

TABLE 7

A = CRa, B = CRb, G = CRe, J = CRf, D = E = M = CH, L = N

| Compound | $R_x$ | $R_a$ | $R_b$ | $R_c$ | $R_d$ | $R_e$ | $R_f$ | Test Example 1 | 3 | 4 |
|---|---|---|---|---|---|---|---|---|---|---|
| 147 | H | H | H | H | $CH_2C(CH_3)_3$ | $COO(CH_2)_3CH_3$ | H | H | $G_B$ | $G_E$ | $G_H$ |

TABLE 8

A = CRa, B = CRb, G = CRe, J = CRf, D = E = L = CH, M = N

| | | | | | | | | Test Example | | |
|---|---|---|---|---|---|---|---|---|---|---|
| Compound | $R_x$ | $R_a$ | $R_b$ | $R_c$ | $R_d$ | $R_e$ | $R_f$ | 1 | 3 | 4 |
| 148 | H | H | H | $CH_2C(CH_3)_3$ | $COO(CH_2)_3CH_3$ | H | H | $G_B$ | $G_E$ | $G_H$ |

TABLE 9

A = CRa, B = CRb, G = CRe, J = CRf, M = CRg, D = E = L = CH

| | | | | | | | | | Test Example | | |
|---|---|---|---|---|---|---|---|---|---|---|---|
| Compound | Rx | Ra | Rb | Rc | Rd | Re | Rf | Rg | 1 | 3 | 4 |
| 149 | H | H | H | $CH_2C(CH_3)_3$ | $COO(CH_2)_3CH_3$ | H | H | $COO(CH_2)_3CH_3$ | $G_B$ | $G_E$ | $G_H$ |
| 150 | H | H | H | $CH_2C(CH_3)_3$ | COOH | H | H | OH | $G_C$ | $G_F$ | $G_I$ |
| 151 | H | H | H | $CH_2C(CH_3)_3$ | COOH | H | H | $NH_2$ | $G_C$ | $G_F$ | $G_I$ |
| 152 | H | H | H | $CH_2C(CH_3)_3$ | COOH | H | H | $CH_3$ | $G_C$ | $G_F$ | $G_I$ |

TABLE 10

A = CRa, B = CRb, G = CRe, J = CRf, L = CRh, D = E = M = CH

| | | | | | | | | | Test Example | | |
|---|---|---|---|---|---|---|---|---|---|---|---|
| Compound | Rx | Ra | Rb | Rc | Rd | Re | Rf | Rh | 1 | 3 | 4 |
| 153 | H | H | H | $CH_2C(CH_3)_3$ | COOH | H | H | OH | $G_B$ | $G_E$ | $G_H$ |
| 154 | H | H | H | $CH_2C(CH_3)_3$ | COOH | H | H | $NH_2$ | $G_B$ | $G_E$ | $G_H$ |
| 155 | H | H | H | $CH_2C(CH_3)_3$ | COOH | H | H | $CH_3$ | $G_B$ | $G_E$ | $G_H$ |

Test Example 2. Evaluation of Cytotoxicity of Stilbene Derivative

The cytotoxicity of the stilbene derivatives was measured. Replicon cells that stably replicate a hepatitis C virus genome were attached to a 96-well plate and cultured in a $CO_2$ incubator at 37° C. for 24 hr. The replicon cells cultured for one day were washed with a phosphate buffered saline (PBS) solution, treated with the compounds of the present invention, and then cultured for 72 hr. Thereafter, through the MTT [3-(4,5-dimethylthiazol-2-yl)-2,5-diphenyltetrazolium bromide] cytotoxicity test, $CC_{50}$ values of the compounds of the present invention were measured. The $CC_{50}$ values of the compounds of the present invention were 200 μM or more. For example, Compound 64 had a $CC_{50}$ of 320 μM, Compound 65 had a $CC_{50}$ of 284 μM, and Compound 66 had a $CC_{50}$ of 245 μM. Accordingly, the compounds of Chemical Formula 1 of the present invention exhibited no cytotoxicity.

Test Example 3. Evaluation of Antiviral Activity of Stilbene Derivative

The antiviral activity of the stilbene derivatives on hepatitis C virus was measured. The replicon cells that stably replicate the hepatitis C virus genome were attached to a culture plate and cultured in a $CO_2$ incubator at 37° C. for 24 hr. The replicon cells cultured for one day were washed with a PBS solution, treated with the compounds of the present invention, and then cultured for 72 hr. The stilbene derivative-treated replicon cells were washed with a cold PBS solution and added with 20 μL of a cell lysis solution so that the cells were lysed in ice for 20 min. 100 μL of a *Renilla luciferase* substrate was added thereto, after which the luminescence thereof was measured and thus the amount of the hepatitis C virus genome was estimated. The amount of the hepatitis C virus genome in the stilbene derivative-treated replicon cells according to the present invention relative to the amount of the hepatitis C virus genome in dimethylsulfoxide (DMSO)-treated replicon cells is shown.

Compounds 1 to 155 of Tables 1 to 10 may be grouped as follows based on the antiviral activity ($EC_{50}$) values:

Group D ($G_D$): $EC_{50}$ of 50 μM or less but exceeding 5 μM,
Group E ($G_E$): $EC_{50}$ of 5 μM or less but exceeding 0.5 μM, and
Group F ($G_F$): $EC_{50}$ of 0.5 μM or less.

Thus, the compounds of Chemical Formula 1 of the present invention exhibited antiviral effects.

Test Example 4. Inhibitory Activity Test on Mitochondrial Swelling

Cyclophilin is a key protein for forming permeability transition pores (PTP) in mitochondria. When permeability transition pores are formed, mitochondria swell, whereby the outer membrane thereof ruptures and thus cell death progresses. Such mitochondrial dysfunction causes many diseases including neurodegenerative diseases, cancer, and the like. Cyclosporine, a known cyclophilin inhibitor, is capable of preventing the formation of permeability transition pores to thus suppress mitochondrial swelling.

The mitochondrial swelling test was performed as follows. Specifically, the hepatocytes were disrupted using a Dounce tissue grinder. The disrupted cells were centrifuged at 700×g for 10 min and the supernatant was transferred into a new tube. The supernatant was centrifuged at 12,000×g for 15 min, thereby obtaining mitochondria.

When the extracted mitochondria were added with calcium, they swelled, which may be observed by measuring the absorbance at 520 nm. The stilbene derivatives are effective at inhibiting mitochondrial swelling due to calcium.

The activity of Compounds 1 to 155 of Tables 1 to 10 on inhibiting mitochondrial swelling may be determined based on $IC_{50}$ values, and may be grouped as follows:

Group G ($G_G$): $IC_{50}$ of 500 μM or less but exceeding 50 μM,

Group H ($G_H$): $IC_{50}$ of 50 μM or less but exceeding 5 μM, and

Group I ($G_I$): $IC_{50}$ of 5 μM or less.

The results of NMR analysis and LCMS analysis of Compounds 1 to 155 corresponding to the stilbene derivatives prepared in Examples 1 and 2 are as follows.

Compound 1:
NMR (400 MHz, $CDCl_3$): 8.03 (d, 1H), 7.84 (s, 1H), 7.63 (d, 2H), 7.37 (m, 1H) 7.27 (m, 2H), 7.10 (m, 2H), 2.78 (s, 6H), 2.42 ppm (s, 3H)
LCMS: $MH^+$=263.1

Compound 2:
NMR (400 MHz, DMSO-$D_6$): 8.41 (s, 1H), 8.05 (d, 1H), 7.78 (m, 2H), 7.62 (m, 3H) 7.36 (d, 2H), 2.65 (m, 2H), 1.20 ppm (m, 3H)
LCMS: $MH^+$=260.1

Compound 3:
NMR (400 MHz, $CDCl_3$): 8.03 (d, 1H), 7.85 (s, 1H), 7.66 (d, 2H), 7.38 (m, 1H) 7.28 (m, 2H), 7.12 (m, 2H), 2.78 (s, 6H), 2.70 (m, 2H), 1.28 ppm (m, 3H)
LCMS: $MNa^+$=300.1

Compound 4:
NMR (400 MHz, $CDCl_3$): 8.11 (m, 1H), 7.87 (s, 1H), 7.65 (d, 2H), 7.47 (d, 1H) 7.39 (m, 2H), 7.27 (s, 2H), 2.98 (m, 1H), 1.29 ppm (d, 6H)
LCMS: $MH^+$=282.0

Compound 5:
NMR (400 MHz, $CDCl_3$): 8.33 (s, 1H), 8.24 (m, 1H), 7.91 (d, 1H), 7.72 (m, 1H) 7.67 (d, 2H), 7.56 (m, 1H), 7.33 (d, 2H), 2.98 (m, 1H), 1.29 ppm (d, 6H)
LCMS: $MNa^+$=314.1

Compound 6:
NMR (400 MHz, $CDCl_3$): 8.13 (d, 1H), 7.93 (s, 1H), 7.63 (m, 2H), 7.41 (m, 1H) 7.31 (m, 2H), 7.27 (m, 1H), 6.94 (d, 1H), 3.89 (s, 3H), 2.97 (m, 1H), 1.28 ppm (d, 6H)
LCMS: $MH^+$=278.1

Compound 7:
NMR (400 MHz, $CDCl_3$): 8.31 (m, 2H), 8.10 (m, 2H), 7.91 (d, 2H), 7.44 (m, 1H) 7.14 (m, 2H), 2.80 ppm (s, 6H)
LCMS: $MH^+$=294.1

Compound 8:
NMR (400 MHz, DMSO-$D_6$): 8.41 (s, 1H), 8.04 (m, 1H), 7.76 (m, 2H), 7.62 (m, 3H) 7.35 (d, 2H), 2.63 (m, 2H), 1.58 (m, 2H), 1.32 (m, 2H), 0.92 ppm (m, 3H)
LCMS: $MH^+$=304.1

Compound 9:
NMR (400 MHz, $CDCl_3$): 8.33 (s, 1H), 8.23 (d, 1H), 7.92 (d, 1H), 7.73 (m, 1H) 7.67 (m, 2H), 7.56 (m, 1H), 7.28 (m, 2H), 2.67 (m, 1H), 1.66 (m, 2H), 1.28 (d, 3H), 0.860 ppm (m, 3H)
LCMS: $MNa^+$=288.1

Compound 10:
NMR (400 MHz, $CDCl_3$): 8.34 (s, 1H), 8.23 (m, 1H), 7.92 (d, 1H), 7.73 (d, 1H) 7.68 (d, 2H), 7.49 (m, 1H), 7.27 (s, 2H), 1.37 ppm (s, 9H)
LCMS: $MNa^+$=328.3

Compound 11:
NMR (400 MHz, $CDCl_3$): 8.15 (d, 1H), 7.95 (s, 1H), 7.64 (d, 2H), 7.46 (d, 2H) 7.27 (s, 1H), 7.07 (m, 1H), 6.94 (d, 1H), 3.89 (s, 3H), 1.36 ppm (s, 9H)
LCMS: $MH^+$=292.2

Compound 12:
NMR (300 MHz, $CDCl_3$): 7.83 (d, 1H), 7.53 (m, 1H), 7.40 (m, 1H), 7.31 (d, 1H) 7.16 (m, 2H), 7.08 (d, 2H), 3.70 (s, 3H), 2.30 ppm (d, 6H)
LCMS: $MH^+$=264.1

Compound 13:
NMR (300 MHz, $CDCl_3$): 7.85 (d, 1H), 7.49 (m, 1H), 7.37 (m, 1H), 7.28 (d, 1H) 7.15 (m, 2H), 7.02 (d, 2H), 2.28 ppm (d, 6H)
LCMS: $MNa^+$=299.1

Compound 14:
NMR (300 MHz, $CDCl_3$): 7.58 (d, 2H), 7.55 (d, 1H), 7.36 (m, 1H), 7.32 (d, 1H) 7.01 (m, 2H), 6.91 (d, 2H), 3.89 (s, 3H), 1.38 ppm (s, 9H)
LCMS: $MH^+$=320.2

Compound 15:
NMR (300 MHz, $CDCl_3$): 7.75 (d, 1H), 7.72 (m, 2H), 7.65 (d, 2H), 7.61 (d, 1H) 7.43 (d, 2H), 7.39 (s, 1H), 1.37 ppm (s, 9H)
LCMS: $MNa^+$=355.1

Compound 16:
NMR (300 MHz, $CDCl_3$): 7.83 (d, 1H), 7.80 (s, 1H), 7.75 (d, 2H), 7.60 (m, 1H) 7.25 (d, 1H), 7.19 (m, 1H), 7.08 (d, 2H), 4.12 (m, 2H), 3.89 (s, 3H), 1.42 ppm (m, 3H)
LCMS: $MH^+$=280.1

Compound 17:
NMR (300 MHz, $CDCl_3$): 7.94 (d, 1H), 7.90 (s, 1H), 7.83 (d, 2H), 7.65 (m, 1H) 7.30 (d, 1H), 7.22 (m, 1H), 7.14 (d, 2H) 4.17 (m, 2H), 1.43 ppm (m, 3H)
LCMS: $MNa^+$=315.1

Compound 18:
NMR (300 MHz, $CDCl_3$): 7.82 (d, 1H), 7.67 (s, 1H), 7.55 (m, 1H), 7.50 (d, 2H) 7.17 (m, 2H), 6.97 (m, 2H), 3.92 (m, 2H), 3.63 (s, 3H), 1.77 (m, 2H), 1.50 (m, 2H), 0.99 ppm (m, 3H)
LCMS: $MH^+$=308.2

Compound 19:
NMR (300 MHz, $CDCl_3$): 7.90 (d, 1H), 7.79 (s, 1H), 7.60 (m, 1H), 7.53 (d, 2H) 7.24 (m, 2H), 7.04 (m, 2H), 4.02 (m, 2H), 1.83 (m, 2H0, 1.57 (m, 2H), 1.01 ppm (m, 3H)
LCMS: $MNa^+$=343.1

Compound 20:
NMR (300 MHz, $CDCl_3$): 7.84 (d, 1H), 7.81 (s, 1H), 7.75 (m, 3H), 7.59 (m, 1H) 7.26 (m, 3H), 7.20 (m, 4H), 7.09 (m, 1H), 4.04 (s, 2H), 3.89 ppm (s, 3H)
LCMS: $MH^+$=326.2

Compound 21:
NMR (300 MHz, $CDCl_3$): 7.86 (d, 1H), 7.82 (s, 1H), 7.78 (m, 3H), 7.59 (m, 1H) 7.28 (m, 3H), 7.23 (m, 4H), 7.11 (m, 1H), 4.09 ppm (s, 2H)
LCMS: $MNa^+$=361.1

Compound 22:
NMR (300 MHz, $CDCl_3$): 8.23 (d, 2H), 8.15 (s, 1H), 7.83 (d, 2H), 7.67 (m, 1H) 7.53 (m, 2H), 7.38 (m, 1H), 2.76 (m, 2H), 1.23 ppm (m, 3H)
LCMS: $MH^+$=279.1

Compound 23:
NMR (300 MHz, CDCl$_3$): 8.22 (d, 2H), 8.16 (s, 1H), 7.84 (d, 2H), 7.66 (m, 1H) 7.53 (m, 2H), 7.37 (m, 1H), 2.96 (m, 1H), 1.24 ppm (d, 6H)
LCMS: MH$^+$=293.1
Compound 24:
NMR (300 MHz, CDCl$_3$): 8.30 (d, 1H), 7.57 (d, 1H), 7.50 (s, 1H), 7.35 (m, 2H) 6.78 (m, 2H), 6.69 (m, 2H), 6.15 ppm (s, 2H)
LCMS: MH$^+$=266.1
Compound 25:
NMR (300 MHz, CDCl$_3$): 8.36 (d, 2H), 8.16 (d, 1H), 8.13 (s, 1H), 7.91 (d, 2H) 7.52 (m, 1H), 7.25 (d, 1H), 7.19 (d, 1H), 3.07 (m, 4H), 2.62 (broad s, 4H), 2.41 ppm (s, 3H)
LCMS: MH$^+$=349.2
Compound 26:
NMR (300 MHz, CDCl$_3$): 8.29 (d, 2H), 8.23 (m, 2H), 7.84 (d, 2H), 7.48 (m, 1H) 7.07 (m, 1H), 7.00 (m, 1H), 4.50 (m, 1H), 1.86 (m, 2H), 1.39 (d, 3H), 1.07 ppm (m, 3H)
LCMS: MH$^+$=323.1
Compound 27:
NMR (300 MHz, CDCl$_3$): 8.38 (d, 2H), 8.28 (m, 1H), 8.24 (s, 1H), 7.88 (d, 2H) 7.64 (m, 1H), 6.84 (m, 1H), 6.69 (d, 1H), 3.93 (d, 2H), 0.92 (m, 1H), 0.72 (m, 2H), 0.42 ppm (m, 2H)
LCMS: MH$^+$=339.1
Compound 28:
NMR (300 MHz, CDCl$_3$): 8.34 (d, 2H), 8.26 (d, 1H), 8.20 (s, 1H), 7.88 (d, 2H) 7.50 (m, 1H), 7.13 (m, 1H), 7.03 (d, 1H), 4.15 (m, 2H), 2.53 (m, 2H), 2.31 ppm (s, 6H)
LCMS: MH$^+$=338.1
Compound 29:
NMR (300 MHz, CDCl$_3$): 8.35 (d, 2H), 8.17 (d, 1H), 8.14 (s, 1H), 7.92 (d, 2H) 7.48 (m, 1H), 7.18 (m, 2H), 2.98 (m, 4H), 1.74 ppm (m, 6H)
LCMS: MH$^+$=334.2
Compound 30:
NMR (300 MHz, CDCl$_3$): 8.36 (d, 2H), 8.18 (d, 1H), 8.15 (s, 1H), 7.91 (d, 2H) 7.55 (m, 1H), 7.26 (m, 1H), 7.19 (d, 1H), 3.89 (m, 4H), 3.03 ppm (m, 4H)
LCMS: MH$^+$=336.1
Compound 31:
NMR (300 MHz, CDCl$_3$): 8.35 (d, 2H), 8.10 (s, 1H), 7.89 (m, 3H), 7.46 (m, 3H) 2.72 (m, 1H), 1.87 (m, 4H), 1.60 ppm (m, 6H)
LCMS: MH$^+$=333.2
Compound 32:
NMR (300 MHz, CDCl$_3$): 8.34 (d, 2H), 7.88 (d, 2H), 7.68 (s, 1H), 7.56 (s, 1H) 7.46 (m, 2H), 7.08 (d, 1H), 4.10 (m, 2H), 1.92 (m, 1H), 1.88 (m, 2H), 1.02 ppm (d, 6H)
LCMS: MH$^+$=337.2
Compound 33:
NMR (300 MHz, CDCl$_3$): 8.27 (d, 2H), 7.82 (d, 2H), 7.64 (s, 1H), 7.52 (s, 1H) 7.41 (m, 3H), 4.07 (m, 2H), 2.48 (m, 2H), 2.28 (d, 6H), 2.03 ppm (m, 2H)
LCMS: MH$^+$=352.2
Compound 34:
NMR (300 MHz, CDCl$_3$): 8.34 (d, 2H), 8.02 (d, 2H), 7.88 (d, 2H), 7.46 (m, 2H) 7.36 (m, 1H), 2.65 (d, 2H), 1.86 (m, 1H), 0.96 ppm (d, 6H)
LCMS: MH$^+$=307.1
Compound 35:
NMR (400 MHz, CDCl$_3$): 8.36 (m, 3H), 8.05 (d, 1H), 7.94 (d, 1H), 7.87 (d, 2H) 7.75 (d, 2H), 7.45 (m, 2H), 2.68 (s, 2H), 0.94 ppm (s, 9H)
LCMS: MH$^+$=321.2

Compound 36:
NMR (300 MHz, CDCl$_3$): 8.35 (d, 2H), 8.02 (d, 2H), 7.90 (d, 2H), 7.39 (m, 3H) 2.76 (m, 2H), 1.67 (m, 1H), 1.52 (m, 2H), 0.98 ppm (d, 6H)
LCMS: MH$^+$=321.2
Compound 37:
NMR (400 MHz, CDCl$_3$): 8.30 (m, 3H), 7.87 (s, 1H), 7.75 (d, 2H), 7.63 (m, 2H) 7.53 (m, 2H), 7.08 (d, 2H), 3.98 ppm (s, 2H)
LCMS: MH$^+$=409.0
Compound 38:
NMR (400 MHz, CDCl$_3$): 8.29 (m, 3H), 7.88 (s, 1H), 7.75 (d, 2H), 7.63 (m, 2H) 7.54 (m, 2H), 7.24 (m, 2H), 7.06 (d, 2H), 3.07 (m, 2H), 2.96 ppm (m, 2H)
LCMS: MH$^+$=355.1
Compound 39:
NMR (300 MHz, CDCl$_3$): 8.34 (d, 2H), 8.27 (d, 1H), 8.02 (d, 2H), 7.88 (d, 2H) 7.46 (m, 1H), 7.35 (m, 1H), 2.77 (m, 2H), 1.83 (m, 5H), 1.55 (m, 2H), 1.34 (m, 4H), 1.02 ppm (m, 2H)
LCMS: MH$^+$=361.2
Compound 40:
NMR (300 MHz, CDCl$_3$): 8.38 (d, 2H), 8.26 (d, 1H), 8.02 (d, 2H), 7.88 (d, 2H), 7.43 (m, 1H), 7.36 (m, 1H), 2.73 (m, 2H), 1.67 (m, 8H), 1.27 (m, 3H), 1.16 (m, 2H), 1.04 ppm (m, 2H)
LCMS: MH$^+$=375.2
Compound 41:
NMR (300 MHz, CDCl$_3$): 8.36 (d, 2H), 8.03 (d, 2H), 7.87 (d, 2H), 7.42 (m, 3H), 2.65 (d, 2H), 1.89 (m, 1H), 1.72 ppm (m, 10H)
LCMS: MH$^+$=347.2
Compound 42:
NMR (300 MHz, CDCl$_3$): 8.33 (d, 2H), 8.02 (d, 1H), 7.79 (s, 1H), 7.70 (d, 2H) 7.47 (m, 1H), 7.40 (d, 2H), 7.30 (m, 5H), 2.7 (m, 4H), 1.99 ppm (m, 2H)
LCMS: MH$^+$=369.2
Compound 43:
NMR (300 MHz, CDCl$_3$): 8.37 (d, 2H), 8.03 (d, 2H), 7.88 (d, 2H), 7.46 (m, 1H) 7.35 (m, 2H), 2.72 (m, 2H), 1.49 (m, 2H), 1.00 ppm (s, 9H)
LCMS: MH$^+$=335.2
Compound 44: LCMS: MH$^+$=385.2
Compound 45: LCMS: MH$^+$=411.2
Compound 46: LCMS: MH$^+$=389.1
Compound 47: LCMS: MH$^+$=389.1
Compound 48: LCMS: MH$^+$=389.1
Compound 49: LCMS: MH$^+$=385.2
Compound 50: LCMS: MH$^+$=385.2
Compound 51: LCMS: MNa$^+$=420.1
Compound 52: LCMS: MH$^+$=369.2
Compound 53: LCMS: MH$^+$=370.2
Compound 54:
NMR (300 MHz, CDCl$_3$): 7.99 (d, 1H), 7.82 (s, 1H), 7.61 (d, 2H), 7.32 (m, 1H) 7.25 (m, 2H), 7.12 (m, 2H), 2.21 (s, 2H), 0.97 ppm (s, 9H)
LCMS: MH$^+$=320.1
Compound 55:
NMR (300 MHz, CDCl$_3$): 8.23 (d, 2H), 7.81 (d, 2H), 7.61 (s, 1H), 7.50 (s, 1H) 7.39 (m, 3H), 2.77 (m, 1H), 2.08 (m, 1H), 1.22 (s, 3H), 0.76 ppm (m, 6H)
LCMS: MH$^+$=320.1
Compound 56:
NMR (300 MHz, CDCl$_3$): 8.19 (d, 1H), 7.83 (s, 1H), 7.63 (d, 2H), 7.54 (m, 1H) 7.45 (m, 2H), 7.37 (m, 2H), 2.99 (m, 1H), 1.32 (m, 3H), 1.03 ppm (s, 9H)
LCMS: MH$^+$=334.1

Compound 57:

NMR (300 MHz, CDCl$_3$): 8.31 (s, 1H), 8.23 (m, 1H), 7.94 (d, 1H), 7.71 (m, 1H) 7.68 (d, 2H), 7.53 (m, 1H), 7.34 (d, 2H), 2.88 (m, 2H), 1.69 (m, 2H), 0.98 ppm (s, 9H)

LCMS: MH$^+$=334.1

Compound 58:

NMR (300 MHz, CDCl$_3$): 8.26 (d, 2H), 7.87 (d, 2H), 7.61 (s, 1H), 7.55 (s, 1H) 7.40 (m, 3H), 2.67 (m, 2H), 2.08 (m, 1H), 1.88 (m, 1H), 0.96 ppm (m, 9H)

LCMS: MH$^+$=334.1

Compound 59:

NMR (300 MHz, CDCl$_3$): 8.35 (s, 1H), 8.24 (m, 1H), 7.91 (d, 1H), 7.73 (m, 1H) 7.66 (d, 2H), 7.57 (m, 1H), 7.38 (d, 2H), 2.65 (d, 2H), 1.77 (m, 1H), 1.71 ppm (m, 10H)

LCMS: MH$^+$=346.1

Compound 60:

NMR (300 MHz, CDCl$_3$): 8.33 (s, 1H), 8.22 (m, 1H), 7.92 (d, 1H), 7.74 (m, 1H) 7.67 (d, 2H), 7.56 (m, 1H), 7.36 (d, 2H), 2.71 (s, 2H), 1.67 (m, 8H), 1.29 (m, 3H), 1.17 (m, 2H), 1.06 ppm (m, 2H)

LCMS: MH$^+$=360.1

Compound 61:

NMR (300 MHz, CDCl$_3$): 8.32 (s, 1H), 8.20 (m, 1H), 7.92 (d, 1H), 7.74 (m, 1H) 7.64 (d, 2H), 7.53 (m, 1H), 7.34 (d, 2H), 2.62 (s, 2H), 1.66 (m, 1H), 0.43 (m, 2H), 0.20 ppm (m, 2H)

LCMS: MH$^+$=304.1

Compound 62:

NMR (300 MHz, CDCl$_3$): 8.34 (s, 1H), 8.21 (m, 1H), 7.94 (d, 1H), 7.74 (m, 1H) 7.65 (d, 2H), 7.53 (m, 1H), 7.35 (d, 2H), 2.67 (s, 2H), 1.69 (m, 2H), 0.40 (m, 3H), 0.15 ppm (m, 2H)

LCMS: MH$^+$=318.1

Compound 63:

NMR (300 MHz, CDCl$_3$): 8.36 (s, 1H), 8.23 (m, 1H), 7.96 (d, 1H), 7.76 (m, 1H) 7.64 (d, 2H), 7.56 (m, 1H), 7.34 (d, 2H), 2.68 (s, 2H), 1.22 (d, 2H), 1.02 (s, 6H), 0.40 (m, 3H), 0.15 ppm (m, 2H)

LCMS: MH$^+$=360.1

Compound 64:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)

LCMS: MH$^+$=351.2

Compound 65:

NMR (400 MHz, CDCl$_3$): 7.93 (d, 1H), 7.74 (d, 1H), 7.59 (m, 1H), 7.48 (d, 2H), 7.35 (m, 1H), 7.13 (d, 2H), 7.00 (d, 1H), 4.36 (m, 2H), 2.53 (s, 2H), 2.46 (s, 3H), 1.79 (m, 2H), 1.51 (m, 2H), 0.99 (m, 3H), 0.98 ppm (s, 9H)

LCMS: MH$^+$=365.2

Compound 66:

NMR (400 MHz, CDCl$_3$): 7.93 (d, 1H), 7.74 (d, 1H), 7.59 (m, 1H), 7.48 (d, 2H), 7.35 (m, 1H), 7.13 (d, 2H), 7.00 (d, 1H), 4.36 (m, 2H), 2.60 (m, 2H), 2.53 (s, 2H), 1.79 (m, 2H), 1.51 (m, 2H), 1.25 (m, 3H), 0.99 (m, 3H), 0.98 ppm (s, 9H)

LCMS: MH$^+$=379.2

Compound 67:

NMR (400 MHz, CDCl$_3$): 7.94 (m, 2H), 7.74 (d, 1H), 7.59 (m, 1H), 7.52 (m, 1H), 7.44 (m, 1H), 7.35 (m, 1H), 7.13 (m, 1H), 7.00 (d, 1H), 4.36 (m, 2H), 2.53 (s, 2H), 2.48 (s, 3H), 1.79 (m, 2H), 1.51 (m, 2H), 0.99 (m, 3H), 0.98 ppm (s, 9H)

LCMS: MH$^+$=365.2

Compound 68:

NMR (400 MHz, CDCl$_3$): 7.94 (m, 2H), 7.74 (d, 1H), 7.59 (m, 1H), 7.52 (m, 1H), 7.44 (m, 1H), 7.35 (m, 1H), 7.13 (m, 1H), 7.00 (d, 1H), 4.36 (m, 2H), 2.60 (m, 2H), 2.53 (s, 2H), 1.79 (m, 2H), 1.51 (m, 2H), 1.25 (m, 3H), 0.99 (m, 3H), 0.98 ppm (s, 9H)

LCMS: MH$^+$=379.2

Compound 69:

NMR (400 MHz, CDCl$_3$): 7.94 (m, 2H), 7.74 (d, 1H), 7.59 (m, 1H), 7.48 (d, 2H), 7.13 (d, 2H), 7.00 (d, 1H), 4.36 (m, 2H), 2.53 (s, 2H), 2.34 (s, 3H), 1.79 (m, 2H), 1.51 (m, 2H), 0.99 (m, 3H), 0.98 ppm (s, 9H)

LCMS: MH$^+$=365.2

Compound 70:

NMR (400 MHz, CDCl$_3$): 7.92 (m, 1H), 7.74 (d, 1H), 7.59 (m, 1H), 7.48 (d, 2H), 7.13 (d, 2H), 7.00 (d, 1H), 4.36 (m, 2H), 2.53 (s, 2H), 2.34 (s, 3H), 2.22 (s, 3H), 1.79 (m, 2H), 1.51 (m, 2H), 0.99 (m, 3H), 0.98 ppm (s, 9H)

LCMS: MH$^+$=379.2

Compound 71:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.36 (m, 2H), 2.53 (s, 2H), 1.85 (m, 2H), 1.05 (m, 3H), 0.94 ppm (s, 9H)

LCMS: MH$^+$=337.2

Compound 72:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.36 (m, 2H), 2.53 (s, 2H), 1.79 (m, 2H), 1.43 (m, 4H), 0.99 (s, 9H), 0.97 ppm (m, 3H)

LCMS: MH$^+$=351.2

Compound 73:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 5.33 (m, 1H), 2.54 (s, 2H), 1.42 (d, 6H), 0.96 ppm (s, 9H)

LCMS: MH$^+$=337.2

Compound 74:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.03 (m, 2H), 2.41 (s, 2H), 2.03 (m, 1H), 1.53 (m, 4H), 1.48 (m, 2H), 1.43 (m, 2H), 1.27 (m, 2H), 0.94 ppm (s, 9H)

LCMS: MH$^+$=391.2

Compound 75:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H4.46 (m, 1H), 4.21 (m, 1H), 3.33 (m, 1H), 2.79 (m, 1H), 2.69 (m, 1H), 2.41 (s, 2H), 1.55 (m, 1H), 1.48 (m, 2H), 1.45 (m, 1H), 0.94 ppm (s, 9H)

LCMS: MH$^+$=392.2

Compound 76:

NMR (400 MHz, CDCl$_3$): 7.94 (m, 2H), 7.74 (d, 1H), 7.59 (m, 1H), 7.47 (m, 4H), 7.38 (m, 4H), 7.13 (d, 2H), 7.00 (d, 1H), 5.26 (m, 2H), 2.53 (s, 2H), 0.98 ppm (s, 9H)

LCMS: MH$^+$=385.2

Compound 77:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 3.91 (m, 1H), 2.53 (s, 2H), 1.99 (m, 2H), 1.74 (m, 2H), 1.53 (m, 2H), 1.48 (m, 2H), 1.43 (m, 2H), 0.94 ppm (s, 9H)

LCMS: MH$^+$=377.2

Compound 78:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.36 (m, 2H), 2.63 (m, 1H), 2.38 (m, 1H), 2.04 (m, 1H), 1.80 (m, 2H), 1.55 (m, 2H), 1.45 (m, 2H), 0.96 (m, 3H), 0.90 ppm (m, 6H)

LCMS: MH$^+$=351.2

Compound 79:
NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.36 (m, 2H), 2.54 (m, 2H), 1.89 (m, 1H), 1.80 (m, 2H), 1.60 (m, 2H), 1.56 (m, 2H), 1.46 (m, 4H), 1.35 (m, 2H), 0.90 ppm (m, 3H)
LCMS: MH$^+$=363.2

Compound 80:
NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.29 (m, 2H), 1.81 (m, 1H), 1.53 (m, 4H), 1.48 (m, 2H), 1.44 (m, 2H), 1.27 (m, 2H), 0.90 ppm (m, 3H)
LCMS: MH$^+$=377.2

Compound 81:
NMR (400 MHz, CDCl$_3$): 7.94 (m, 2H), 7.74 (d, 1H), 7.59 (m, 1H), 7.48 (d, 2H), 7.35 (m, 3H), 7.23 (m, 3H), 7.13 (d, 2H), 7.00 (d, 1H), 4.36 (m, 2H), 1.79 (m, 2H), 1.51 (m, 2H), 0.90 ppm (m, 3H)
LCMS: MH$^+$=371.2

Compound 82:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.42 (m, 5H), 1.80 (m, 2H), 1.45 (m, 2H), 0.94 (s, 9H), 0.90 ppm (m, 3H)
LCMS: MH$^+$=365.2

Compound 83:
NMR (400 MHz, CDCl$_3$): 7.92 (m, 1H), 7.59 (m, 1H), 7.48 (d, 2H), 7.35 (m, 1H), 7.13 (d, 2H), 7.00 (d, 1H), 4.36 (m, 2H), 2.48 (s, 3H), 2.42 (m, 5H), 1.80 (m, 2H), 1.45 (m, 2H), 0.94 (s, 9H), 0.90 ppm (m, 3H)
LCMS: MH$^+$=379.2

Compound 84:
NMR (400 MHz, CDCl$_3$): 7.94 (m, 2H), 7.59 (m, 1H), 7.50 (m, 1H), 7.46 (m, 1H), 7.35 (m, 1H), 7.13 (m, 1H), 7.00 (d, 1H), 4.36 (m, 2H), 2.48 (s, 3H), 2.42 (m, 5H), 1.80 (m, 2H), 1.45 (m, 2H), 0.94 (s, 9H), 0.90 ppm (m, 3H)
LCMS: MH$^+$=379.2

Compound 85:
NMR (400 MHz, CDCl$_3$): 7.94 (m, 2H), 7.59 (m, 1H), 7.48 (d, 2H), 7.13 (d, 2H), 7.00 (d, 1H), 4.36 (m, 2H), 2.42 (m, 5H), 2.34 (s, 3H), 1.80 (m, 2H), 1.45 (m, 2H), 0.94 (s, 9H), 0.90 ppm (m, 3H)
LCMS: MH$^+$=379.2

Compound 86:
NMR (400 MHz, CDCl$_3$): 7.92 (m, 1H), 7.59 (m, 1H), 7.48 (d, 2H), 7.13 (d, 2H), 7.00 (d, 1H), 4.36 (m, 2H), 2.42 (m, 5H), 2.34 (s, 3H), 2.22 (s, 3H), 1.80 (m, 2H), 1.45 (m, 2H), 0.94 (s, 9H), 0.90 ppm (m, 3H)
LCMS: MH$^+$=393.2

Compound 87:
NMR (400 MHz, CDCl$_3$): 77.94 (m, 2H), 7.59 (m, 1H), 7.48 (d, 2H), 7.35 (m, 1H), 7.13 (d, 2H), 7.00 (d, 1H), 4.36 (m, 2H), 2.42 (m, 5H), 1.91 (m, 2H), 0.94 (s, 9H), 0.90 ppm (m, 3H)
LCMS: MH$^+$=351.2

Compound 88:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.42 (m, 5H), 1.80 (m, 2H), 1.39 (m, 2H), 1.31 (m, 2H), 0.94 (s, 9H), 0.90 ppm (m, 3H)
LCMS: MH$^+$=379.2

Compound 89:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 5.33 (m, 1H), 2.54 (s, 2H), 2.42 (m, 3H), 1.42 (d, 6H), 0.96 ppm (s, 9H)
LCMS: MH$^+$=351.2

Compound 90:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.42 (m, 5H), 2.03 (m, 1H), 1.53 (m, 4H), 1.43 (m, 2H), 1.27 (m, 2H), 1.48 (m, 2H), 0.94 ppm (s, 9H)
LCMS: MH$^+$=405.2

Compound 91:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 3.33 (m, 1H), 2.79 (m, 1H), 2.69 (m, 1H), 2.42 (m, 5H), 1.55 (m, 1H), 1.48 (m, 2H), 1.45 (m, 1H), 0.94 ppm (s, 9H)
LCMS: MH$^+$=406.3

Compound 92:
NMR (400 MHz, CDCl$_3$): 7.94 (m, 2H), 7.59 (m, 1H), 7.48 (m, 4H) 7.36 (m, 4H), 7.13 (d, 2H), 7.00 (d, 1H), 5.26 (m, 2H), 2.53 (s, 2H), 0.98 ppm (s, 9H)
LCMS: MH$^+$=399.2

Compound 93:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 3.91 (m, 1H), 2.42 (s, 2H), 1.99 (m, 2H), 1.74 (m, 2H), 1.53 (m, 2H), 1.48 (m, 2H), 1.43 (m, 2H), 0.94 ppm (s, 9H)
LCMS: MH$^+$=391.3

Compound 94:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.63 (m, 1H), 2.42 (m, 3H), 2.38 (m, 1H), 2.04 (m, 1H), 1.80 (m, 2H), 1.55 (m, 2H), 1.45 (m, 2H), 0.96 (m, 3H), 0.90 ppm (m, 6H)
LCMS: MH$^+$=365.2

Compound 95:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.54 (m, 2H), 2.42 (m, 3H), 1.89 (m, 1H), 1.80 (m, 2H), 1.60 (m, 2H), 1.56 (m, 2H), 1.46 (m, 4H), 1.35 (m, 2H), 0.90 ppm (m, 3H)
LCMS: MH$^+$=377.2

Compound 96:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.42 (m, 3H), 1.81 (m, 3H), 1.53 (m, 4H), 1.48 (m, 2H), 1.44 (m, 4H), 0.90 ppm (m, 3H)
LCMS: MH$^+$=391.2

Compound 97:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.53 (s, 2H), 2.48 (s, 3H), 1.79 (m, 2H), 1.51 (m, 2H), 0.92 ppm (m, 3H)
LCMS: MH$^+$=385.2

Compound 98:
NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 4.36 (m, 2H), 2.53 (s, 2H), 2.02 (s, 2H), 1.79 (m, 2H), 1.51 (m, 2H), 0.99 (m, 3H), 0.98 ppm (s, 9H)
LCMS: MH$^+$=366.2

Compound 99:
NMR (400 MHz, CDCl$_3$): 7.94 (m, 1H), 7.63 (m, 1H), 7.49 (d, 2H), 7.36 (m, 1H), 7.17 (d, 2H), 6.84 (m, 1H), 4.36 (m, 2H), 2.53 (s, 2H), 2.48 (s, 3H), 2.02 (s, 2H), 1.79 (m, 2H), 1.51 (m, 2H), 0.99 (m, 3H), 0.98 ppm (s, 9H)
LCMS: MH$^+$=380.2

Compound 100:

NMR (400 MHz, CDCl$_3$): 7.98 (m, 2H), 7.63 (m, 1H), 7.48 (m, 1H), 7.36 (m, 1H), 7.17 (m, 1H), 6.84 (m, 1H), 4.36 (m, 2H), 2.53 (s, 2H), 2.48 (s, 3H), 2.02 (s, 2H), 1.79 (m, 2H), 1.51 (m, 2H), 0.99 (m, 3H), 0.98 ppm (s, 9H)

LCMS: MH$^+$=380.3

Compound 101:

NMR (400 MHz, CDCl$_3$): 7.98 (m, 2H), 7.63 (m, 1H), 7.49 (d, 2H), 7.17 (d, 2H), 6.84 (m, 1H), 4.36 (m, 2H), 2.53 (s, 2H), 2.34 (s, 3H), 2.02 (s, 2H), 1.79 (m, 2H), 1.51 (m, 2H), 0.99 (m, 3H), 0.98 ppm (s, 9H)

LCMS: MH$^+$=380.3

Compound 102:

NMR (400 MHz, CDCl$_3$): 7.96 (m, 1H), 7.63 (m, 1H), 7.49 (d, 2H), 7.17 (d, 2H), 6.84 (m, 1H), 4.36 (m, 2H), 2.53 (s, 2H), 2.34 (s, 3H), 2.22 (s, 3H), 2.02 (s, 2H), 1.79 (m, 2H), 1.51 (m, 2H), 0.99 (m, 3H), 0.98 ppm (s, 9H)

LCMS: MH$^+$=394.3

Compound 103:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 4.36 (m, 2H), 2.53 (s, 2H), 2.02 (s, 2H), 1.79 (m, 2H), 1.50 (m, 4H), 0.98 (s, 9H), 0.96 ppm (m, 3H)

LCMS: MH$^+$=380.3

Compound 104:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 5.33 (m, 1H), 2.54 (s, 2H), 2.02 (s, 2H), 1.43 (d, 6H), 0.96 ppm (s, 9H)

LCMS: MH$^+$=352.2

Compound 105:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 4.03 (m, 2H), 2.53 (s, 2H), 2.02 (s, 3H), 1.52 (m, 4H), 1.48 (m, 2H), 1.43 (m, 2H), 1.27 ppm (m, 2H)

LCMS: MH$^+$=406.3

Compound 106:

NMR (400 MHz, CDCl$_3$): 7.98 (m, 2H), 7.63 (m, 1H), 7.49 (m, 4H), 7.36 (m, 4H), 7.17 (d, 2H), 6.84 (m, 1H), 5.26 (m, 2H), 2.53 (s, 2H), 2.02 (s, 2H), 0.98 ppm (s, 9H)

LCMS: MH$^+$=400.2

Compound 107:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 3.91 (m, 1H), 2.53 (s, 2H), 2.02 (s, 2H), 1.99 (m, 2H), 1.74 (m, 2H), 1.53 (m, 2H), 1.48 (m, 2H), 1.43 (m, 1H), 0.98 ppm (s, 9H)

LCMS: MH$^+$=392.3

Compound 108:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 4.36 (m, 2H), 2.63 (m, 1H), 2.38 (m, 1H), 2.02 (m, 3H), 1.79 (m, 2H), 1.55 (m, 2H), 1.51 (m, 2H), 0.96 (m, 3H), 0.92 ppm (m, 6H)

LCMS: MH$^+$=366.2

Compound 109:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 4.36 (m, 2H), 2.53 (d, 2H), 2.02 (s, 2H), 1.89 (m, 1H), 1.79 (m, 2H), 1.57 (m, 4H), 1.51 (m, 2H), 1.40 (m, 4H), 0.99 ppm (m, 3H)

LCMS: MH$^+$=378.2

Compound 110:

NMR (400 MHz, CDCl$_3$): 7.98 (m, 2H), 7.63 (m, 1H), 7.49 (d, 2H), 7.36 (m, 1H), 7.17 (d, 2H), 6.84 (m, 1H), 4.36 (m, 2H), 2.53 (d, 2H), 2.02 (s, 2H), 1.80 (m, 3H), 1.51 (m, 6H), 1.48 (m, 2H), 1.43 (m, 2H), 0.98 (m, 3H)

LCMS: MH$^+$=392.3

Compound 111:

NMR (400 MHz, CDCl$_3$): 7.98 (m, 2H), 7.63 (m, 1H), 7.49 (d, 2H), 7.36 (m, 3H), 7.23 (m, 3H), 7.17 (d, 2H), 6.84 (m, 1H), 4.36 (m, 2H), 3.96 (s, 2H), 2.02 (s, 2H), 1.79 (m, 2H), 1.51 (m, 2H), 0.98 ppm (m, 3H)

LCMS: MH$^+$=386.2

Compound 112:

NMR (400 MHz, CDCl$_3$): 7.97 (m, 2H), 7.62 (m, 1H), 7.48 (d, 2H), 7.36 (m, 1H), 7.17 (d, 2H), 6.90 (m, 1H), 4.36 (m, 2H), 2.53 (s, 2H), 1.79 (m, 2H), 1.51 (m, 2H), 0.99 (m, 3H), 0.98 ppm (s, 9H)

LCMS: MH$^+$=369.2

Compound 113:

NMR (400 MHz, CDCl$_3$): 7.92 (m, 1H), 7.59 (m, 1H), 7.48 (d, 2H), 7.35 (m, 1H), 7.13 (d, 2H), 7.00 (m, 1H), 4.36 (m, 2H), 2.53 (s, 2H), 2.48 (s, 3H), 1.79 (m, 2H), 1.51 (m, 2H), 0.99 (m, 3H), 0.98 ppm (s, 9H)

LCMS: MH$^+$=399.2

Compound 114:

NMR (400 MHz, CDCl$_3$): 7.94 (m, 2H), 7.59 (m, 1H), 7.50 (m, 1H), 7.46 (m, 1H), 7.35 (m, 1H), 7.13 (m, 1H), 7.00 (d, 1H), 4.36 (m, 2H), 2.53 (s, 2H), 2.48 (s, 3H), 1.79 (m, 2H), 1.51 (m, 2H), 0.99 (m, 3H), 0.98 ppm (s, 9H)

LCMS: MH$^+$=443.2

Compound 115:

NMR (400 MHz, CDCl$_3$): 7.94 (m, 2H), 7.59 (m, 1H), 7.48 (d, 2H), 7.13 (d, 2H), 7.00 (d, 1H), 4.36 (m, 2H), 2.53 (s, 2H), 2.34 (s, 3H), 1.79 (m, 2H), 1.51 (m, 2H), 0.99 (m, 3H), 0.98 ppm (s, 9H)

LCMS: MH$^+$=491.1

Compound 116:

NMR (400 MHz, CDCl$_3$): 7.94 (m, 1H), 7.62 (m, 1H), 7.48 (d, 2H), 7.17 (d, 2H), 6.90 (m, 1H), 4.36 (m, 2H), 2.53 (s, 2H), 2.34 (s, 3H), 2.22 (s, 3H), 1.79 (m, 2H), 1.51 (m, 2H), 0.99 (m, 3H), 0.98 ppm (s, 9H)

LCMS: MH$^+$=397.3

Compound 117:

NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.54 (s, 2H), 1.79 (m, 2H), 1.48 (m, 4H), 0.98 (s, 9H), 0.96 ppm (m, 3H)

LCMS: MH$^+$=399.2

Compound 118:

NMR (400 MHz, CDCl$_3$): 7.94 (m, 2H), 7.59 (m, 1H), 7.48 (m, 1H), 7.35 (d, 2H), 7.00 (d, 1H), 5.33 (m, 1H), 2.53 (s, 2H), 1.42 (d, 6H), 0.96 ppm (s, 9H)

LCMS: MH$^+$=415.1

Compound 119:

NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.03 (m, 2H), 2.41 (s, 2H), 2.03 (m, 1H), 1.53 (m, 4H), 1.48 (m, 2H), 1.43 (m, 2H), 1.27 (m, 2H), 0.94 ppm (s, 9H)

LCMS: MH$^+$=517.2

Compound 120:

NMR (400 MHz, CDCl$_3$): 7.97 (m, 2H), 7.62 (m, 1H), 7.47 (m, 4H), 7.37 (m, 4H), 7.17 (d, 2H), 6.90 (m, 1H), 5.26 (m, 2H), 2.42 (s, 2H), 0.94 ppm (s, 9H)

LCMS: MH$^+$=403.2

Compound 121:

NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 3.91

(m, 1H), 2.53 (s, 2H), 1.99 (m, 2H), 1.74 (m, 2H), 1.49 (m, 4H), 1.43 (m, 3H), 0.96 ppm (s, 9H)
LCMS: MH$^+$=411.2

Compound 122:
NMR (400 MHz, CDCl$_3$): 7.94 (m, 2H), 7.59 (m, 1H), 7.48 (d, 2H), 7.35 (m, 1H), 7.13 (d, 2H), 7.00 (d, 1H), 4.36 (m, 2H), 2.63 (m, 1H), 2.38 (m, 1H), 1.79 (m, 2H), 1.51 (m, 2H), 0.99 (m, 3H), 0.96 ppm (m, 6H)
LCMS: MH$^+$=429.1

Compound 123:
NMR (400 MHz, CDCl$_3$): 7.94 (m, 2H), 7.59 (m, 1H), 7.48 (d, 2H), 7.34 (m, 3H), 7.24 (m, 3H), 7.13 (d, 2H), 7.00 (d, 1H), 4.36 (m, 2H), 3.96 (s, 2H), 1.79 (m, 2H), 1.51 (m, 2H), 0.98 ppm (m, 3H)
LCMS: MH$^+$=497.1

Compound 124:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 3.96 (s, 3H), 2.53 (s, 2H), 0.94 ppm (m, 9H)
LCMS: MH$^+$=309.2

Compound 125:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 3.95 (s, 3H), 2.63 (m, 1H), 2.38 (m, 1H), 1.65 (m, 1H), 1.21 (m, 2H), 0.94 (m, 3H), 0.87 ppm (d, 3H)
LCMS: MH$^+$=309.2

Compound 126:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 3.95 (s, 3H), 2.63 (m, 2H), 2.11 (m, 1H), 1.65 ppm (m, 6H)
LCMS: MH$^+$=321.2

Compound 127:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 3.92 (s, 3H), 2.48 (d, 2H), 2.14 (m, 1H), 1.24 ppm (m, 10H)
LCMS: MH$^+$=335.2

Compound 128:
NMR (400 MHz, CDCl$_3$): 7.94 (m, 2H), 7.74 (d, 1H), 7.59 (m, 1H), 7.48 (d, 2H) 7.34 (m, 3H), 7.25 (m, 3H), 7.13 (d, 2H), 7.00 (d, 1H), 3.92 (s, 3H), 3.89 ppm (s, 2H)
LCMS: MH$^+$=329.2

Compound 129:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 3.93 (s, 3H), 2.48 (d, 2H), 1.88 (m, 1H), 0.91 ppm (d, 6H)
LCMS: MH$^+$=295.2

Compound 130:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 3.92 (s, 3H), 2.60 (m, 2H), 1.62 (m, 2H), 1.33 (m, 4H), 0.90 ppm (m, 3H)
LCMS: MH$^+$=309.2

Compound 131:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 4.35 (m, 2H), 2.49 (d, 2H), 1.91 (m, 1H), 1.78 (m, 2H), 1.50 (m, 2H), 0.95 (m, 3H), 0.91 ppm (d, 6H)
LCMS: MH$^+$=337.2

Compound 132:
NMR (400 MHz, CDCl$_3$): 7.94 (m, 2H), 7.74 (d, 1H), 7.59 (m, 1H), 7.48 (d, 2H) 7.35 (m, 1H), 7.13 (d, 2H), 7.00 (d, 1H), 4.37 (m, 2H), 2.64 (m, 2H), 1.85 (m, 2H), 1.68 (m, 2H), 1.53 (m, 2H), 1.37 (m, 4H), 098 (m, 3H), 0.92 ppm (m, 3H)
LCMS: MH$^+$=351.2

Compound 133:
NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 2.53 (s, 2H), 3.27 (m, 4H), 1.92 (m, 4H), 0.96 ppm (s, 9H)
LCMS: MH$^+$=364.2

Compound 134:
NMR (400 MHz, CDCl$_3$): 8.11 (m, 2H), 7.78 (d, 1H), 7.65 (m, 1H), 7.52 (d, 2H), 7.37 (m, 1H), 7.17 (d, 2H), 7.06 (d, 1H), 2.54 (s, 2H), 0.96 ppm (s, 9H)
LCMS: MH$^+$=295.2

Compound 135:
NMR (400 MHz, CDCl$_3$): 8.07 (d, 1H), 7.78 (d, 1H), 7.59 (m, 1H), 7.52 (d, 2H), 7.17 (d, 2H), 7.06 (d, 1H), 6.84 (m, 1H), 2.54 (s, 2H), 0.96 ppm (s, 9H)
LCMS: MH$^+$=311.2

Compound 136:
NMR (400 MHz, CDCl$_3$): 8.09 (m, 2H), 7.78 (d, 1H), 7.52 (d, 2H), 7.17 (d, 2H), 7.07 (m, 2H), 2.54 (s, 2H), 0.96 ppm (s, 9H)
LCMS: MH$^+$=311.2

Compound 137:
NMR (400 MHz, CDCl$_3$): 8.07 (d, 1H), 7.78 (d, 1H), 7.60 (m, 1H), 7.52 (d, 2H), 7.17 (d, 2H), 7.13 (m, 1H), 7.06 (d, 1H), 6.55 (s, 2H), 2.54 (s, 2H), 0.96 ppm (s, 9H)
LCMS: MH$^+$=310.2

Compound 138:
NMR (400 MHz, CDCl$_3$): 8.06 (m, 2H), 7.78 (d, 1H), 7.52 (d, 2H), 7.41 (m, 1H), 7.17 (d, 2H), 7.06 (d, 1H), 6.55 (s, 2H), 2.54 (s, 2H), 0.96 ppm (s, 9H)
LCMS: MH$^+$=310.2

Compound 139:
NMR (400 MHz, CDCl$_3$): 8.07 (d, 1H), 7.78 (d, 1H), 7.59 (m, 1H), 7.52 (d, 2H), 7.21 (m, 1H), 7.17 (d, 2H), 7.06 (d, 1H), 2.54 (s, 2H), 2.48 (s, 3H), 0.96 ppm (s, 9H)
LCMS: MH$^+$=309.2

Compound 140:
NMR (400 MHz, CDCl$_3$): 8.04 (m, 2H), 7.78 (d, 1H), 7.55 (m, 1H), 7.52 (d, 2H), 7.17 (d, 2H), 7.06 (d, 1H), 2.54 (s, 2H), 2.34 (s, 3H), 0.96 ppm (s, 9H)
LCMS: MH$^+$=309.2

Compound 141:
NMR (400 MHz, CDCl$_3$): 7.72 (d, 1H), 7.59 (m, 2H), 7.47 (m, 1H), 7.46 (d, 2H), 7.32 (m, 1H), 7.13 (d, 2H), 7.07 (d, 1H), 6.60 (s, 1H), 6.10 (s, 1H), 2.53 (s, 2H), 0.95 ppm (s, 9H)
LCMS: MH$^+$=294.2

Compound 142:
NMR (400 MHz, CDCl$_3$): 8.34 (s, 1H), 8.17 (m, 1H), 8.04 (m, 2H), 7.74 (m, 3H), 7.48 (d, 2H), 7.13 (d, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)
LCMS: MH$^+$=401.2

Compound 143:
NMR (400 MHz, CDCl$_3$): 8.37 (s, 1H), 7.94 (m, 2H), 7.74 (d, 1H), 7.59 (m, 1H), 7.48 (m, 1H), 7.35 (m, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)
LCMS: MH$^+$=352.2

Compound 144:
NMR (400 MHz, CDCl$_3$): 8.39 (s, 1H), 7.94 (m, 2H), 7.74 (d, 1H), 7.59 (m, 1H), 7.48 (m, 1H), 7.35 (m, 1H), 7.13 (m, 1H), 7.00 (d, 1H), 4.36 (m, 2H), 2.53 (s, 2H), 1.79 (m, 2H), 1.51 (m, 2H), 0.99 (m, 3H), 0.98 ppm (s, 9H)
LCMS: MH$^+$=352.2

Compound 145:

NMR (400 MHz, CDCl$_3$): 8.61 (m, 1H), 7.92 (m, 1H), 7.74 (d, 1H), 7.59 (m, 1H), 7.48 (d, 2H), 7.13 (d, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)

LCMS: MH$^+$=352.2

Compound 146:

NMR (400 MHz, CDCl$_3$): 9.17 (s, 1H), 8.27 (m, 1H), 7.94 (m, 1H), 7.74 (d, 1H), 7.48 (d, 2H), 7.13 (d, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)

LCMS: MH$^+$=352.2

Compound 147:

NMR (400 MHz, CDCl$_3$): 8.90 (s, 1H), 8.00 (m, 1H), 7.94 (d, 1H), 7.74 (d, 1H), 7.48 (d, 2H), 7.13 (d, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)

LCMS: MH$^+$=352.2

Compound 148:

NMR (400 MHz, CDCl$_3$): 8.76 (m, 1H), 7.94 (m, 1H), 7.74 (d, 1H), 7.48 (d, 2H), 7.35 (m, 1H), 7.13 (d, 2H), 7.00 (d, 1H), 4.36 (m, 2H), 2.53 (s, 2H), 1.79 (m, 2H), 1.51 (m, 2H), 0.99 (m, 3H), 0.98 ppm (s, 9H)

LCMS: MH$^+$=352.2

Compound 149:

NMR (400 MHz, CDCl$_3$): 7.94 (m, 2H), 7.74 (d, 1H), 7.59 (m, 1H), 7.48 (d, 2H), 7.35 (m, 1H), 7.13 (d, 2H), 7.00 (d, 1H), 4.36 (m, 4H), 2.53 (s, 2H), 1.79 (m, 4H), 1.51 (m, 4H), 0.99 (m, 6H), 0.98 ppm (s, 9H)

LCMS: MH$^+$=451.3

Compound 150:

NMR (400 MHz, CDCl$_3$): 8.15 (d, 1H), 7.78 (d, 1H), 7.52 (d, 2H), 7.31 (m, 1H), 7.17 (d, 2H), 7.06 (d, 1H), 7.12 (m, 1H), 2.54 (s, 2H), 0.96 ppm (s, 9H)

LCMS: MH$^+$=311.2

Compound 151:

NMR (400 MHz, CDCl$_3$): 8.15 (d, 1H), 7.78 (d, 1H), 7.52 (d, 2H), 7.41 (m, 1H), 7.32 (m, 1H), 7.17 (d, 2H), 7.06 (d, 1H), 6.55 (s, 2H), 2.54 (s, 2H), 0.96 ppm (s, 9H)

LCMS: MH$^+$=310.2

Compound 152:

NMR (400 MHz, CDCl$_3$): 8.15 (d, 1H), 7.78 (d, 1H), 7.52 (d, 2H), 7.49 (m, 1H), 7.29 (m, 1H), 7.17 (d, 2H), 7.06 (d, 1H), 2.54 (s, 2H), 2.48 (s, 3H), 0.96 ppm (s, 9H)

LCMS: MH$^+$=309.2

Compound 153:

NMR (400 MHz, CDCl$_3$): 8.09 (m, 2H), 7.78 (d, 1H), 7.52 (d, 2H), 7.17 (d, 2H), 7.06 (d, 1H), 6.81 (m, 1H), 2.54 (s, 2H), 0.96 ppm (s, 9H)

LCMS: MH$^+$=311.2

Compound 154:

NMR (400 MHz, CDCl$_3$): 8.10 (m, 2H), 7.78 (d, 1H), 7.52 (d, 2H), 7.17 (d, 2H), 7.14 (m, 1H), 7.06 (d, 1H), 6.55 (s, 2H), 2.54 (s, 2H), 0.96 ppm (s, 9H)

LCMS: MH$^+$=310.2

Compound 155:

NMR (400 MHz, CDCl$_3$): 8.10 (m, 2H), 7.78 (d, 1H), 7.52 (d, 2H), 7.21 (m, 1H), 7.17 (d, 2H), 7.06 (d, 1H), 2.54 (s, 2H), 2.34 (s, 3H), 0.96 ppm (s, 9H)

LCMS: MH$^+$=309.2

INDUSTRIAL APPLICABILITY

The novel stilbene derivatives of the present invention can be used as an inhibitor of the function of cyclophilin, which has an improved pharmaceutical profile.

The invention claimed is:

1. A compound represented by Chemical Formula 1 below or a pharmaceutically acceptable salt thereof:

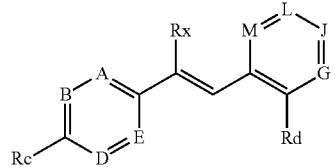

[Chemical Formula 1]

in Chemical Formula 1,
A is CRa,
B is CRb,
G is CRe,
J is CRf,
M is CRg,
D, E, and L are CRh,
Rx is H,
Ra is hydrogen, or a C1-C5 alkyl group,
Rb is hydrogen,
Rc is —CH$_2$C(CH$_3$)$_3$,
Rd is COOH or —COOR5 (R5 is a C1-C10 alkyl group or a C3-C10 cycloalkyl group, wherein the C1-C10 alkyl group may be substituted with at least one substituent selected from the group consisting of amine, a C6-C12 aryl, a C5-C10 heterocyclic group including nitrogen as a hetero atom, and a C3-C10 cycloalkyl group),
Re is hydrogen, NH$_2$, OH, or a C1-C10 alkyl group,
Rf is hydrogen, NH$_2$, OH, or a C1-C4 alkyl group,
Rg is hydrogen, NH$_2$, OH, a C1-C10 alkyl group, or —COORz (Rz is a C1-C10 alkyl group), and
Rh is hydrogen, NH$_2$, OH, or a C1-C5 alkyl group.

2. A compound represented by Chemical Formula 1 below or the pharmaceutically acceptable salt thereof:

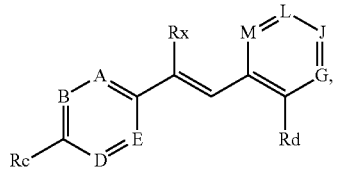

[Chemical Formula 1]

wherein the compound is at least one selected from the group consisting of Compounds 64-77, 124, 134-140, 142, and 149-155 below:

| A = CRa, B = CRb, G = CRe, D = E = L = M = CH ||||||||
| Compound | Rx | Ra | Rb | Rc | Rd | Re | Rf |
| --- | --- | --- | --- | --- | --- | --- | --- |
| 64 | H | H | H | $CH_2C(CH_3)_3$ | $COO(CH_2)_3CH_3$ | H | H |
| 65 | H | H | H | $CH_2C(CH_3)_3$ | $COO(CH_2)_3CH_3$ | $CH_3$ | H |
| 66 | H | H | H | $CH_2C(CH_3)_3$ | $COO(CH_2)_3CH_3$ | $CH_2CH_3$ | H |
| 67 | H | $CH_3$ | H | $CH_2C(CH_3)_3$ | $COO(CH_2)_3CH_3$ | H | H |
| 68 | H | $CH_2CH_3$ | H | $CH_2C(CH_3)_3$ | $COO(CH_2)_3CH_3$ | H | H |
| 69 | H | H | H | $CH_2C(CH_3)_3$ | $COO(CH_2)_3CH_3$ | H | $CH_3$ |
| 70 | H | H | H | $CH_2C(CH_3)_3$ | $COO(CH_2)_3CH_3$ | $CH_3$ | $CH_3$ |
| 71 | H | H | H | $CH_2C(CH_3)_3$ | $COO(CH_2)_3CH_3$ | H | H |
| 72 | H | H | H | $CH_2C(CH_3)_3$ | $COO(CH_2)_3CH_3$ | H | H |
| 73 | H | H | H | $CH_2C(CH_3)_3$ | $COO(CH_2)_3CH_3$ | H | H |
| 74 | H | H | H | $CH_2C(CH_3)_3$ | –C(=O)O–CH$_2$–cyclohexyl | H | H |
| 75 | H | H | H | $CH_2C(CH_3)_3$ | –C(=O)O–CH$_2$–(piperidin-2-yl) | H | H |
| 76 | H | H | H | $CH_2C(CH_3)_3$ | $COOCH_2Ph$ | H | H |
| 77 | H | H | H | $CH_2C(CH_3)_3$ | –C(=O)O–cyclohexyl | H | H |
| 124 | H | H | H | $CH_2C(CH_3)_3$ | COOH | H | H |
| 134 | H | H | H | $CH_2C(CH_3)_3$ | COOH | H | H |
| 135 | H | H | H | $CH_2C(CH_3)_3$ | COOH | OH | H |
| 136 | H | H | H | $CH_2C(CH_3)_3$ | COOH | H | CH |
| 137 | H | H | H | $CH_2C(CH_3)_3$ | COOH | $NH_2$ | H |
| 138 | H | H | H | $CH_2C(CH_3)_3$ | COOH | H | $NH_2$ |
| 139 | H | H | H | $CH_2C(CH_3)_3$ | COOH | $CH_3$ | H |
| 140 | H | H | H | $CH_2C(CH_3)_3$ | COOH | H | $CH_3$ |

| A = CRa, B = CRb, G = CRe, D = E = M = CH |||||||
| | Rx | Ra | Rb | Rc | Rd | Re | Fused ring formation of J and L |
| --- | --- | --- | --- | --- | --- | --- | --- |
| 142 | H | H | H | $CH_2C(CH_3)_3$ | $COO(CH_2)_3CH_3$ | H | benzene (ortho-fused) |

| A = CRa, B = CRb, G = CRe, J = CRf, M = CRg, D = E = L = CH ||||||||
| | Rx | Ra | Rb | Rc | Rd | Re | Rf | Rg |
| --- | --- | --- | --- | --- | --- | --- | --- | --- |
| 149 | H | H | H | $CH_2C(CH_3)_3$ | $COO(CH_2)_3CH_3$ | H | H | $COO(CH_2)_3CH_3$ |
| 150 | H | H | H | $CH_2C(CH_3)_3$ | COOH | H | H | OH |
| 151 | H | H | H | $CH_2C(CH_3)_3$ | COOH | H | H | $NH_2$ |
| 152 | H | H | H | $CH_2C(CH_3)_3$ | COOH | H | H | $CH_3$ |

| A = CRa, B = CRb, G = CRe, J = CRf, L = CRh, D = E = L = CH ||||||||
| | Rx | Ra | Rb | Rc | Rd | Re | Rf | Rh |
| --- | --- | --- | --- | --- | --- | --- | --- | --- |
| 153 | H | H | H | $CH_2C(CH_3)_3$ | COOH | H | H | OH |
| 154 | H | H | H | $CH_2C(CH_3)_3$ | COOH | H | H | $NH_2$ |
| 155 | H | H | H | $CH_2C(CH_3)_3$ | COOH | H | H | $CH_3$. |

3. A method of inhibiting activities of cyclophilin in a subject, the method comprising:
administering, to a subject in need of such inhibition, an effective amount of a composition comprising a compound represented by Chemical Formula 1 below or a pharmaceutically acceptable salt thereof:

[Chemical Fomula 1]

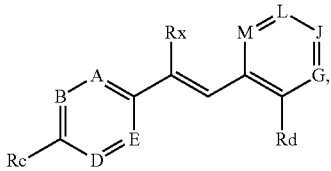

in Chemical Formula 1,
A is CRa,
B is CRb,
G is CRe,
J is CRf,
M is CRg,
D, E, and L are CRh,
Rx is H,
Ra is hydrogen, or a C1-C5 alkyl group,
Rb is hydrogen,
Rc is a —$CH_2C(CH_3)_3$,
Rd is COOH, or —COOR5 (R5 is a C1-C10 alkyl group or a C3-C10 cycloalkyl group, wherein the C1-C10 alkyl group may be substituted with at least one substituent selected from the group consisting of amine, a C6-C12 aryl, a C5-C10 heterocyclic group including nitrogen as a hetero atom, and a C3-C10 cycloalkyl group),
Re is hydrogen, $NH_2$, OH, or a C1-C10 alkyl group,
Rf is hydrogen, $NH_2$, OH, or a C1-C4 alkyl group,
Rg is hydrogen, $NH_2$, OH, a C1-C10 alkyl group, or —COORz (Rz is a C1-C20 alkyl group), and
Rh is hydrogen, $NH_2$, OH, or a C1-C5 alkyl group.

4. The method of claim 3, wherein the method is to treat at least one cyclophilin-related disease selected from the group consisting of an infectious disease, a cardiovascular disease, rheumatoid arthritis, sepsis, asthma, periodontitis, aging, alopecia, a neurodegenerative disease, and cancer.

5. The method of claim 3, wherein the compound is at least one selected from the group consisting of Compounds 64-77, 124, 134-140, 142 and 149-155 below:

| | | | | A = CRa, B = CRb, G = CRe, D = E = L = M = CH | | | |
|---|---|---|---|---|---|---|---|
| Compound | Rx | Ra | Rb | Rc | Rd | Re | Rf |
| 64 | H | H | H | $CH_2C(CH_3)_3$ | $COO(CH_2)_3CH_3$ | H | H |
| 65 | H | H | H | $CH_2C(CH_3)_3$ | $COO(CH_2)_3CH_3$ | $CH_3$ | H |
| 66 | H | H | H | $CH_2C(CH_3)_3$ | $COO(CH_2)_3CH_3$ | $CH_2CH_3$ | H |
| 67 | H | $CH_3$ | H | $CH_2C(CH_3)_3$ | $COO(CH_2)_3CH_3$ | H | H |
| 68 | H | $CH_2CH_3$ | H | $CH_2C(CH_3)_3$ | $COO(CH_2)_3CH_3$ | H | H |
| 69 | H | H | H | $CH_2C(CH_3)_3$ | $COO(CH_2)_3CH_3$ | H | $CH_3$ |
| 70 | H | H | H | $CH_2C(CH_3)_3$ | $COO(CH_2)_3CH_3$ | $CH_3$ | $CH_3$ |
| 71 | H | H | H | $CH_2C(CH_3)_3$ | $COO(CH_2)_3CH_3$ | H | H |
| 72 | H | H | H | $CH_2C(CH_3)_3$ | $COO(CH_2)_3CH_3$ | H | H |
| 73 | H | H | H | $CH_2C(CH_3)_3$ | $COO(CH_2)_3CH_3$ | H | H |
| 74 | H | H | H | $CH_2C(CH_3)_3$ | (cyclohexylmethyl ester) | H | H |
| 75 | H | H | H | $CH_2C(CH_3)_3$ | (piperidinylmethyl ester) | H | H |
| 76 | H | H | H | $CH_2C(CH_3)_3$ | $COOCH_2Ph$ | H | H |
| 77 | H | H | H | $CH_2C(CH_3)_3$ | (cyclohexyl ester) | H | H |
| 124 | H | H | H | $CH_2C(CH_3)_3$ | COOH | H | H |
| 134 | H | H | H | $CH_2C(CH_3)_3$ | COOH | H | H |
| 135 | H | H | H | $CH_2C(CH_3)_3$ | COOH | OH | H |
| 136 | H | H | H | $CH_2C(CH_3)_3$ | COOH | H | CH |
| 137 | H | H | H | $CH_2C(CH_3)_3$ | COOH | $NH_2$ | H |
| 138 | H | H | H | $CH_2C(CH_3)_3$ | COOH | H | $NH_2$ |
| 139 | H | H | H | $CH_2C(CH_3)_3$ | COOH | $CH_3$ | H |
| 140 | H | H | H | $CH_2C(CH_3)_3$ | COOH | H | $CH_3$ |

-continued

| | | | | | | | Fused ring |
|---|---|---|---|---|---|---|---|
| | Rx | Ra | Rb | Rc | Rd | Re | formation of J and L |

A = CRa, B = CRb, G = CRe, D = E = M = CH

| 142 | H | H | H | CH$_2$C(CH$_3$)$_3$ | COO(CH$_2$)$_3$CH$_3$ | H | 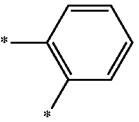 [SMILES: *c1ccccc1*] |

A = CRa, B = CRb, G = CRe, J = CRf, M = CRg, D = E = L = CH

| ... | Rx | Ra | Rb | Rc | Rd | Re | Rf | Rg |
|---|---|---|---|---|---|---|---|---|
| 149 | H | H | H | CH$_2$C(CH$_3$)$_3$ | COO(CH$_2$)$_3$CH$_3$ | H | H | COO(CH$_2$)$_3$CH$_3$ |
| 150 | H | H | H | CH$_2$C(CH$_3$)$_3$ | COOH | H | H | OH |
| 151 | H | H | H | CH$_2$C(CH$_3$)$_3$ | COOH | H | H | NH$_2$ |
| 152 | H | H | H | CH$_2$C(CH$_3$)$_3$ | COOH | H | H | CH$_3$ |

A = CRa, B = CRb, G = CRe, J = CRf, L = CRh, D = E = L = CH

| ... | Rx | Ra | Rb | Rc | Rd | Re | Rf | Rh |
|---|---|---|---|---|---|---|---|---|
| 153 | H | H | H | CH$_2$C(CH$_3$)$_3$ | COOH | H | H | OH |
| 154 | H | H | H | CH$_2$C(CH$_3$)$_3$ | COOH | H | H | NH$_2$ |
| 155 | H | H | H | CH$_2$C(CH$_3$)$_3$ | COOH | H | H | CH$_3$. |

\* \* \* \* \*